(12) United States Patent
Nakatani et al.

(10) Patent No.: US 9,500,589 B2
(45) Date of Patent: Nov. 22, 2016

(54) SAMPLE HOLDING CARRIER AND FLUORESCENCE DETECTION DEVICE USING SAME

(71) Applicants: PANASONIC CORPORATION, Osaka (JP); SANYO ELECTRIC CO., LTD., Osaka (JP)

(72) Inventors: Morio Nakatani, Miyagi (JP); Masaya Nakatani, Hyogo (JP); Yoshiyuki Matsumura, Osaka (JP); Kenji Nagatomi, Osaka (JP); Akio Oki, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 14/514,048

(22) Filed: Oct. 14, 2014

(65) Prior Publication Data

US 2015/0031121 A1 Jan. 29, 2015

Related U.S. Application Data

(63) Continuation of application No. PCT/JP2013/060454, filed on Apr. 5, 2013.

(30) Foreign Application Priority Data

Apr. 25, 2012 (JP) .................................. 2012-100414
May 11, 2012 (JP) .................................. 2012-110069

(51) Int. Cl.
*G01N 21/64* (2006.01)
*G01N 21/27* (2006.01)

(52) U.S. Cl.
CPC ........ *G01N 21/6452* (2013.01); *G01N 21/645* (2013.01); *G01N 21/6428* (2013.01); *G01N 21/6486* (2013.01); *G01N 21/274* (2013.01); *G01N 2021/6439* (2013.01)

(58) Field of Classification Search
CPC ..................... G01N 21/6452; G01N 21/6428; G01N 21/6486; G01N 21/272; G01N 21/64; G01N 21/8507; G01N 2021/7773; G01N 2021/2021; G01N 2021/7786; G01N 2021/7796; G01N 21/554; G01N 33/582; G01N 33/58; G01N 33/6452
USPC ................. 422/82.07, 82.08, 554; 435/288.7
See application file for complete search history.

(56) References Cited

U.S. PATENT DOCUMENTS 6,242,114 B1 * 6/2001 Yamasaki ................. B32B 7/02
250/461.2
6,361,672 B1 * 3/2002 Zhu et al. ..................... 204/603
(Continued)

FOREIGN PATENT DOCUMENTS

JP 2001-208689 A 8/2001
JP 2001208689 * 8/2001
(Continued)

OTHER PUBLICATIONS

International Search Report issued in PCT/JP2013/060454, dated Jul. 16, 2013, with English translation.
(Continued)

*Primary Examiner* — Jyoti Nagpaul
(74) *Attorney, Agent, or Firm* — McDermott Will & Emery LLP

(57) ABSTRACT

Disclosed is a sample holding carrier allowing samples to be measured accurately, and a fluorescence detection device for use with the sample holding carrier. A biosensor substrate includes a base substrate, a plurality of wells formed on a first surface side of the base substrate; and grooves formed on the first surface side of the base substrate separately from the wells and generating fluorescence under exposure to excitation light. The fluorescence detection device applies excitation light to the grooves, thereby figuring out the level of the fluorescence to be detected from the biosensor substrate. As a result, the fluorescence detection device can amplify the detection signals of the fluorescence generated when the excitation light is applied to the wells to an appropriate level, thereby accurately detecting the fluorescence generated in the samples.

19 Claims, 23 Drawing Sheets

(56) References Cited

U.S. PATENT DOCUMENTS

| | | |
|---|---|---|
| 2002/0150503 A1 | 10/2002 | Tanaka et al. |
| 2005/0048595 A1* | 3/2005 | Yamatsu et al. ............... 435/18 |
| 2005/0226779 A1 | 10/2005 | Oldham et al. |
| 2005/0287040 A1* | 12/2005 | Giebeler et al. ........... 422/82.08 |
| 2006/0128030 A1* | 6/2006 | Mamine et al. .............. 436/518 |
| 2006/0171288 A1* | 8/2006 | Kuypers .................... 369/275.1 |
| 2006/0215526 A1* | 9/2006 | Worthington ......... B01L 3/5027 369/100 |
| 2006/0275181 A1* | 12/2006 | Takeda et al. ................ 422/102 |
| 2006/0275182 A1* | 12/2006 | Hudson ................ B01L 3/5085 422/400 |
| 2007/0070344 A1 | 3/2007 | Sugiyama et al. |
| 2009/0104354 A1 | 4/2009 | Sugiyama et al. |
| 2009/0312195 A1 | 12/2009 | Eliseev |
| 2011/0189723 A1 | 8/2011 | Yamamura et al. |

FOREIGN PATENT DOCUMENTS

| | | |
|---|---|---|
| JP | 2005-003450 A | 1/2005 |
| JP | 2006-153639 A | 6/2006 |
| JP | 2006-322819 A | 11/2006 |
| JP | 2007-093248 A | 4/2007 |
| JP | 2007-263967 A | 10/2007 |
| JP | 2009-204451 A | 9/2009 |
| JP | 2009204451 * | 9/2009 |
| WO | 2010-027003 A1 | 3/2010 |

OTHER PUBLICATIONS

The Extended European Search Report dated Apr. 10, 2015 for the related European Patent Application No. 13781940.5.

* cited by examiner

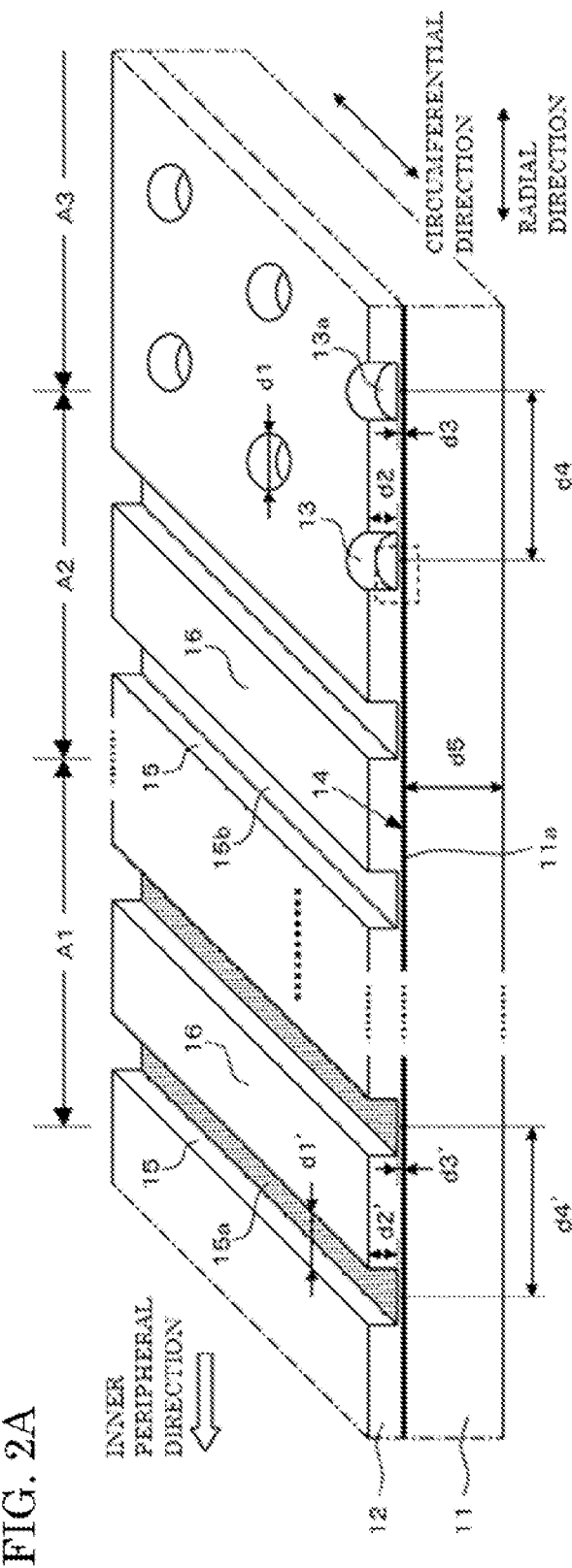
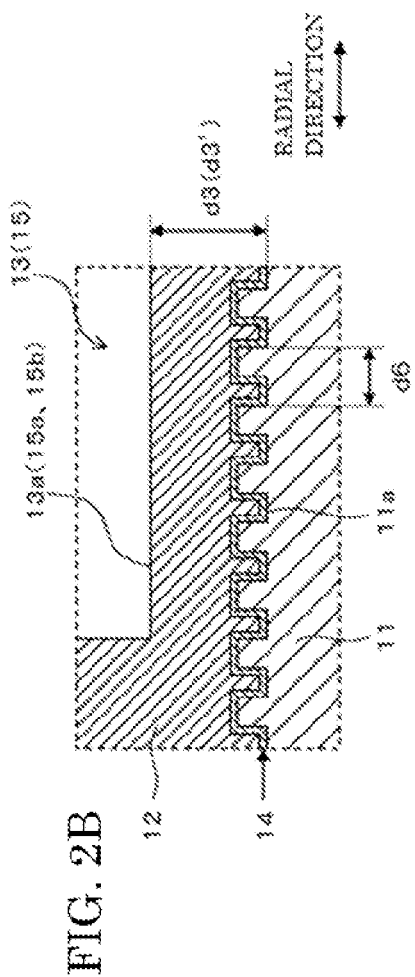
FIG. 2A
FIG. 2B

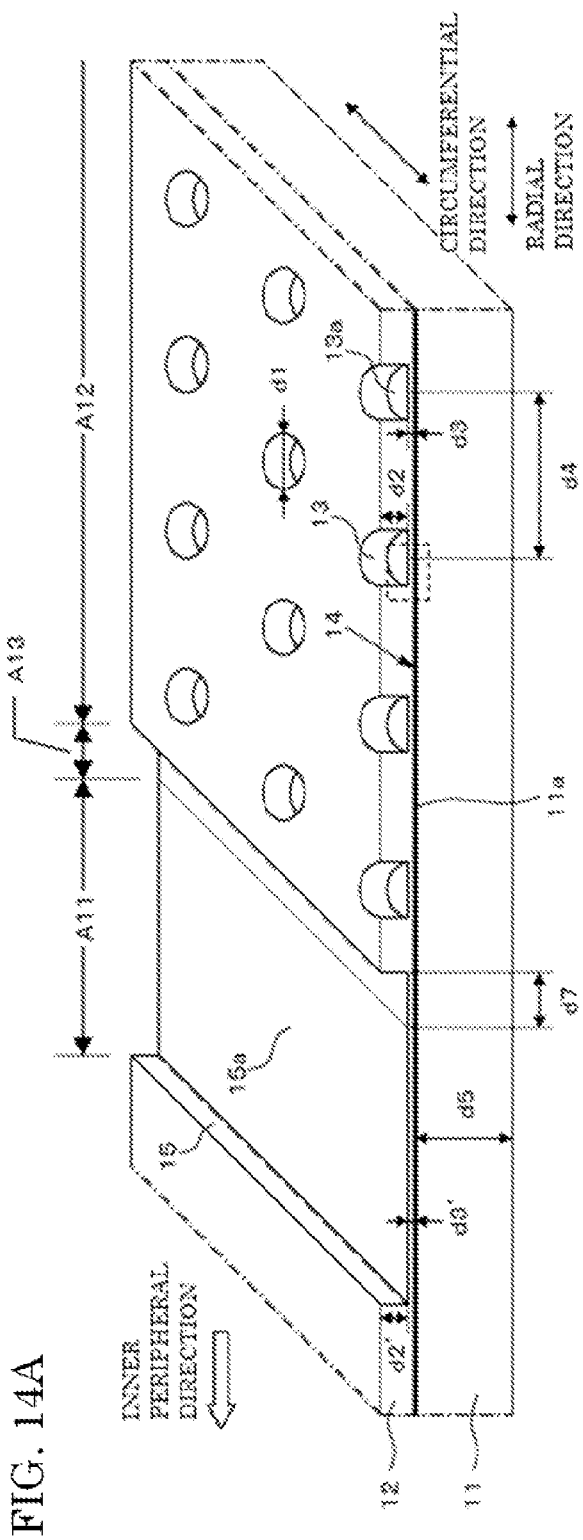
FIG. 14A
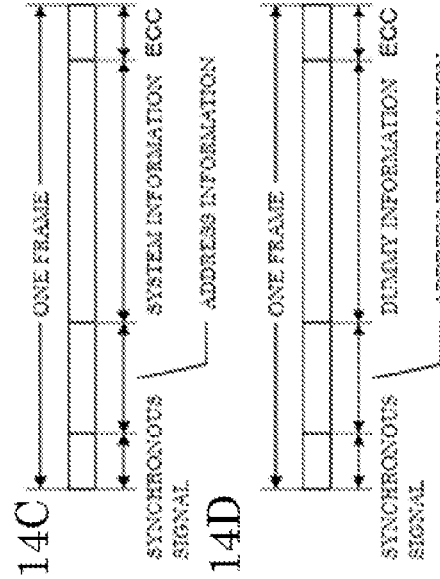
FIG. 14C
FIG. 14D
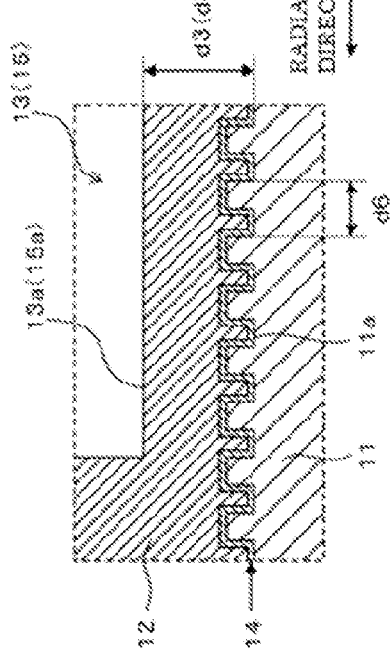
FIG. 14B

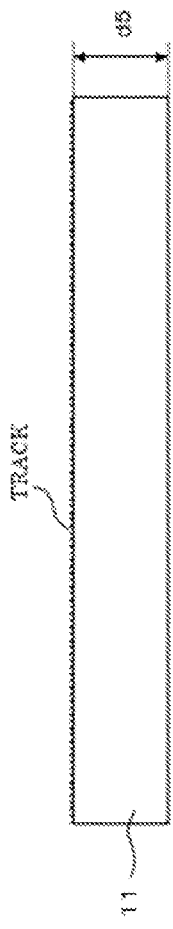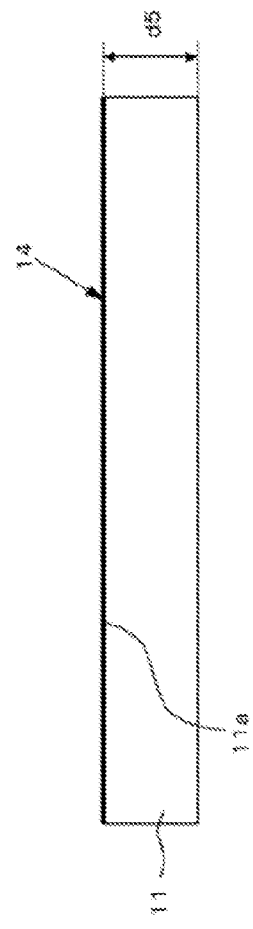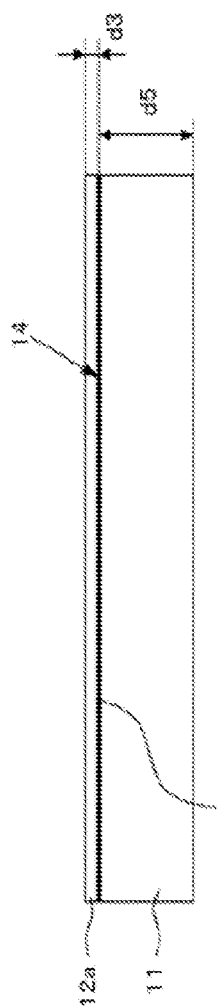

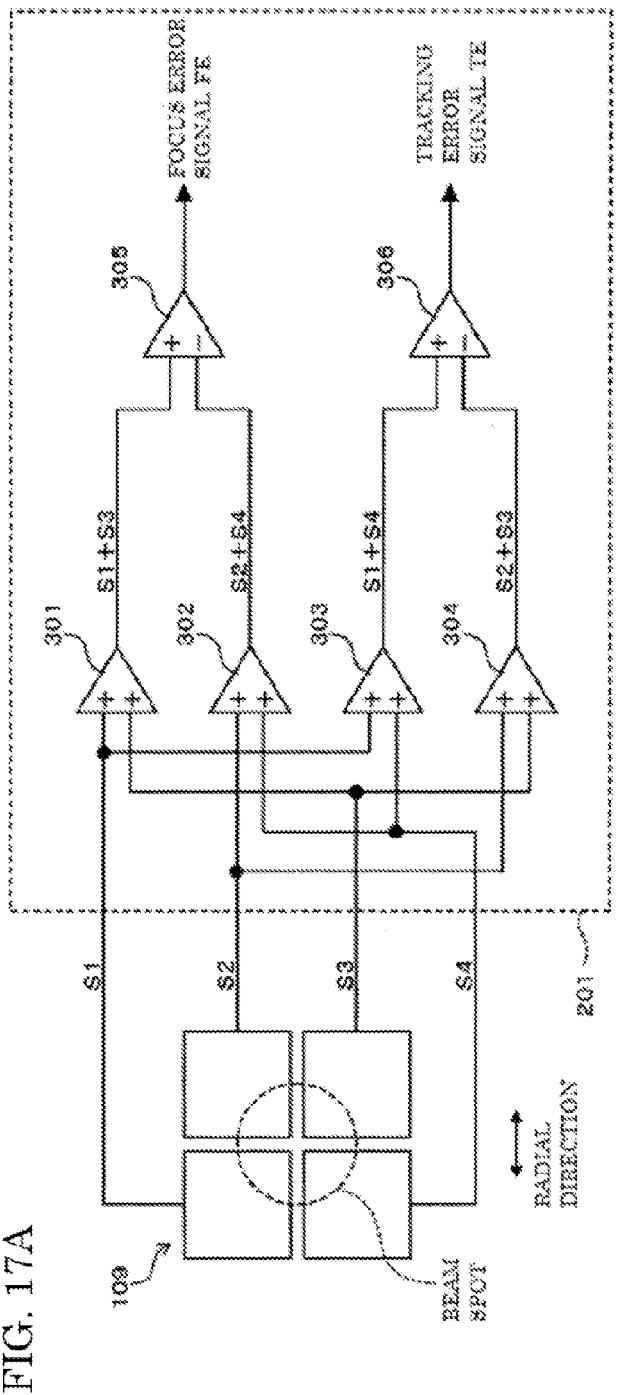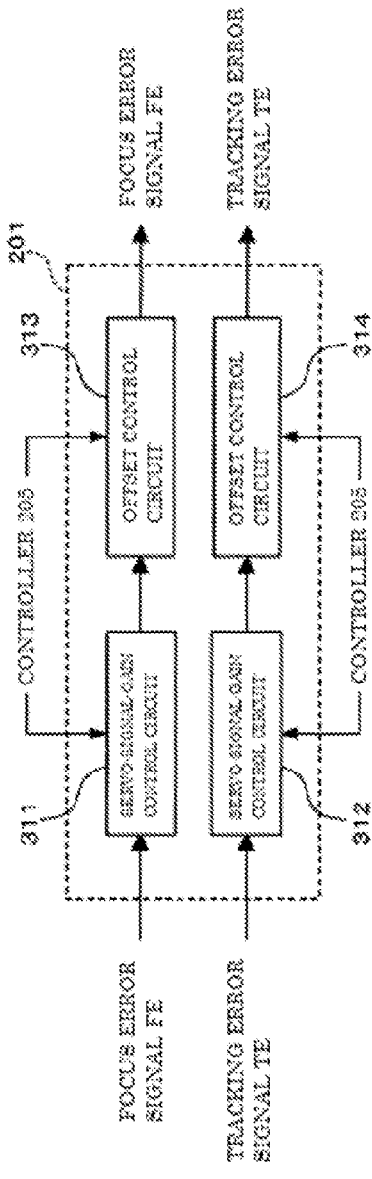
FIG. 17A
FIG. 17B

SAMPLE HOLDING CARRIER AND FLUORESCENCE DETECTION DEVICE USING SAME

RELATED APPLICATIONS

This application is a continuation of International Application No. PCT/JP2013/060454, filed on Apr. 5, 2013, which in turn claims the benefit of Japanese Application No. 2012-100414, filed on Apr. 25, 2012 and Japanese Application No. 2012-110069, filed on May 11, 2012, the disclosures of which Applications are incorporated by reference herein.

TECHNICAL FIELD

The present invention relates to a sample holding carrier for holding samples prepared by fluorescently-labeled test objects such as cells, and also relates to a fluorescence detection device for use with the sample holding carrier.

BACKGROUND ART

Particularly, in medical fields such as a clinical site, it is necessary to detect a cell infected with a pathogen or a cell having a predetermined mode from many cells. For example, WO 2010/027003 discloses a technique of rapidly, simply, and accurately detecting the cell. In the technique of WO 2010/027003, plural micro chambers (wells) are formed on a micro chip array, and each well is filled with fluorescently-labeled cells. Each well is observed with a fluorescent microscope while irradiated with a laser beam, and thereby a specific cell that yields fluorescence is detected.

Unexamined Japanese Patent Publication No. 2006-322819 discloses a configuration in which a series of wells filled with the cells is scanned with the laser beam to detect the fluorescence yielded from the cell. In the configuration of Unexamined Japanese Patent Publication No. 2006-322819, the series of wells is formed in a circumferential direction of a disk, and a series of information pits is formed on a layer on a light incident side separated from a layer in which the well is formed, the series of information pits being formed into a track shape so as to be arranged along an array of the wells. Address information is held in the information pit.

In this configuration, the optical system for detecting fluorescence includes different light sources: one for irradiating the wells with excitation light, and the other for irradiating the information pits with laser light. The light emitted from these light sources is converged by a common object lens. The object lens is controlled so that the laser light for the information pits is focused on the information pits and follows the series of information pits (track). As a result, the excitation light is focused on the cells placed in the wells, and the array of the wells is sequentially scanned with the laser light.

The optical system further includes a light detector for detecting fluorescence generated in cells, and a light detector for receiving laser light modulated by the information pits. The output of the light detector for receiving the laser light is formed into a signal for controlling the object lens and a signal for reproducing the information stored in the information pits.

When the fluorescence is yielded from the cell irradiated with the excitation light, the fluorescence is detected by the photodetector that detects the fluorescence. A position of the well in which the cell yielding the fluorescence is accommodated is identified by positional information that is acquired from the information pit in detecting the fluorescence. The existence or non-existence of a detection target cell and the position of the well in which the cell is accommodated are automatically detected from many cells accommodated in the series of wells provided on the disk without the fluorescence microscope observation.

SUMMARY OF THE INVENTION

Technical Problems

The above-mentioned Japanese Unexamined Patent Publication No. 2006-322819, however, has the following problems. First, the fluorescence intensity acquirable at the time of detection may differ due, for example, to variations in devices (such as light sources used for detection) or use environments. In this case, if the fluorescence intensity acquired from samples is small, the fluorescence may not be detected, thereby decreasing the detection accuracy of the fluorescence.

Another problem is as follows. The information pits can store not only the positional information but also information that is used in detecting fluorescence yielded from a cell as a test object (system information). The system information should be acquired with high accuracy from the information pits. When, however, the wells are formed on the information pits in which the system information is stored, the light reflected by the wells may act as noise, degrading the reproduction signal of the information pits, making it impossible to acquire accurate system information. It is preferable that the optical system be adjusted to optimize the reproduction of the information pits so as to ensure the acquisition of the positional information. Accurate reproduction can be achieved by adjusting the optical system while the reproduction signal of the pit information is acquired by the fluorescence detection device. In this case, however, the light reflected by the wells may act as noise during the adjustment, making accurate adjustment impossible.

In view of these circumstances, an object of the present invention is to provide a sample holding carrier allowing samples to be measured accurately, and also to provide a fluorescence detection device for use with the sample holding carrier.

Another object of the present invention is to provide a sample holding carrier allowing the acquisition of accurate information used at the time of detecting fluorescent generated in a test object, and also to provide a fluorescence detection device for use with the sample holding carrier.

Solution to Problems

A first aspect of the present invention is directed to a sample holding carrier. The sample holding carrier of this aspect includes a substrate; a plurality of sample accommodation units arranged on a first surface side of the substrate; and a fluorescent portion arranged on the first surface side of the substrate separately from the sample accommodation units and generating fluorescence under exposure to irradiation light.

The sample holding carrier of this aspect includes a fluorescent portion which certainly generates fluorescence. Therefore, the fluorescence detection device can figure out the level of the fluorescence to be detected from the sample holding carrier by applying irradiation light to the fluorescent portion. As a result, the fluorescence detection device can amplify the detection signals of the fluorescence generated when the irradiation light is applied to the sample accommodation units to an appropriate level, thereby properly and accurately detecting the fluorescence generated from the samples.

A second aspect of the present invention is directed to a fluorescence detection device that irradiates a sample holding carrier holding a fluorescently-labeled sample with irradiation light and detects fluorescence yielded from the sample irradiated with the irradiation light. The sample holding carrier of this aspect comprises: a substrate; a plurality of sample accommodation units arranged on a first surface side of the substrate; and a fluorescent portion formed on the first surface side of the substrate separately from the sample accommodation units and generating fluorescence under exposure to the irradiation light. The fluorescence detection device of this aspect includes a light source for emitting the irradiation light; an object lens for converging the irradiation light on the sample holding carrier; a fluorescence detector for receiving the fluorescence generated from the samples or from the fluorescent portion by exposure to the irradiation light; and an amplification rate setting unit for setting amplification rate of a signal sent from the fluorescence detector based on the signal sent from the fluorescence detector when the fluorescent portion is exposed to the irradiation light.

As described above, the fluorescence detection device of this aspect can figure out the level of the fluorescence to be detected from the sample holding carrier by applying irradiation light to the fluorescent portion. As a result, the fluorescence detection device can amplify the detection signals of the fluorescence generated when the irradiation light is applied to the sample accommodation units to an appropriate level, thereby properly and accurately detecting the fluorescence generated from the samples.

A third aspect of the present invention is directed to a sample holding carrier. The sample holding carrier of this aspect comprises a substrate; a track formed on a first surface side of the substrate; and a plurality of sample accommodation units formed on the first surface side of the substrate. The first surface side of the substrate is provided with a first region not including the sample accommodation units and a second region including the sample accommodation units; and system information is stored in the track at a portion corresponding to the first region.

In the sample holding carrier of this aspect, the system information is stored in the track at a portion corresponding to the first region not including the sample accommodation units. This allows the reproduction signal of the system information to be less superimposed by noise caused when the irradiation light scans the sample accommodation units in order to read the system information. As a result, the system information can be accurately acquired.

A fourth aspect of the present invention is directed to a fluorescence detection device that irradiates a sample holding carrier holding a fluorescently-labeled sample with irradiation light and detects fluorescence yielded from the sample irradiated with the irradiation light. The sample holding carrier comprises: a substrate; a track formed on a first surface side of the substrate; and a plurality of sample accommodation units formed on the first surface side of the substrate. The first surface side of the substrate is provided with a first region not including the sample accommodation units and a second region including the sample accommodation units; and system information is stored in the track at a portion corresponding to the first region. The fluorescence detection device of this aspect comprises: a light source for emitting the irradiation light; an object lens for converging the irradiation light on the sample holding carrier; a light detector for receiving the irradiation light reflected by the sample holding carrier; a fluorescence detector for receiving the fluorescence generated from the samples by exposure to the irradiation light; and an information acquiring unit for acquiring the system information based on a signal sent from the light detector when the first region is exposed to the irradiation light.

In the fluorescence detection device of this aspect, the system information is stored in the track at a portion corresponding to the first region not including the sample accommodation units. This allows the reproduction signal of the system information to be less superimposed by noise caused when the irradiation light scans the sample accommodation units in order to read the system information. As a result, the system information can be accurately acquired.

Advantageous Effects of Invention

As described above, the present invention provides a sample holding carrier allowing samples to be measured accurately, and also provides a fluorescence detection device for use with the sample holding carrier. The present invention further provides a sample holding carrier allowing the acquisition of accurate information used at the time of detecting fluorescent generated in a test object, and also to provide a fluorescence detection device for use with the sample holding carrier.

The advantageous effects and meanings of the present invention will be more apparent by the following description of the exemplary embodiments. However, the following exemplary embodiments are described only by way of example, but the present invention is not limited to the exemplary embodiments.

BRIEF DESCRIPTION OF DRAWINGS

FIGS. 2A and 2B are a partial perspective view and a partially enlarged sectional view, respectively, of the biosensor substrate of the first embodiment.

FIG. 14A is a partial perspective view of the biosensor substrate, FIG. 14B is a partially enlarged sectional view of the biosensor substrate, and FIGS. 14C and 14D are conceptual views of information stored in a track in the third embodiment.

FIGS. 15A-15D show how to form the biosensor substrate of the third embodiment.

FIGS. 17A and 17B are circuit configurations of a signal calculating circuit in the third embodiment.

DESCRIPTION OF EMBODIMENTS

Embodiments of the present invention will now be described as follows with reference to the accompanying drawings.

<First Embodiment>

Figure 1:
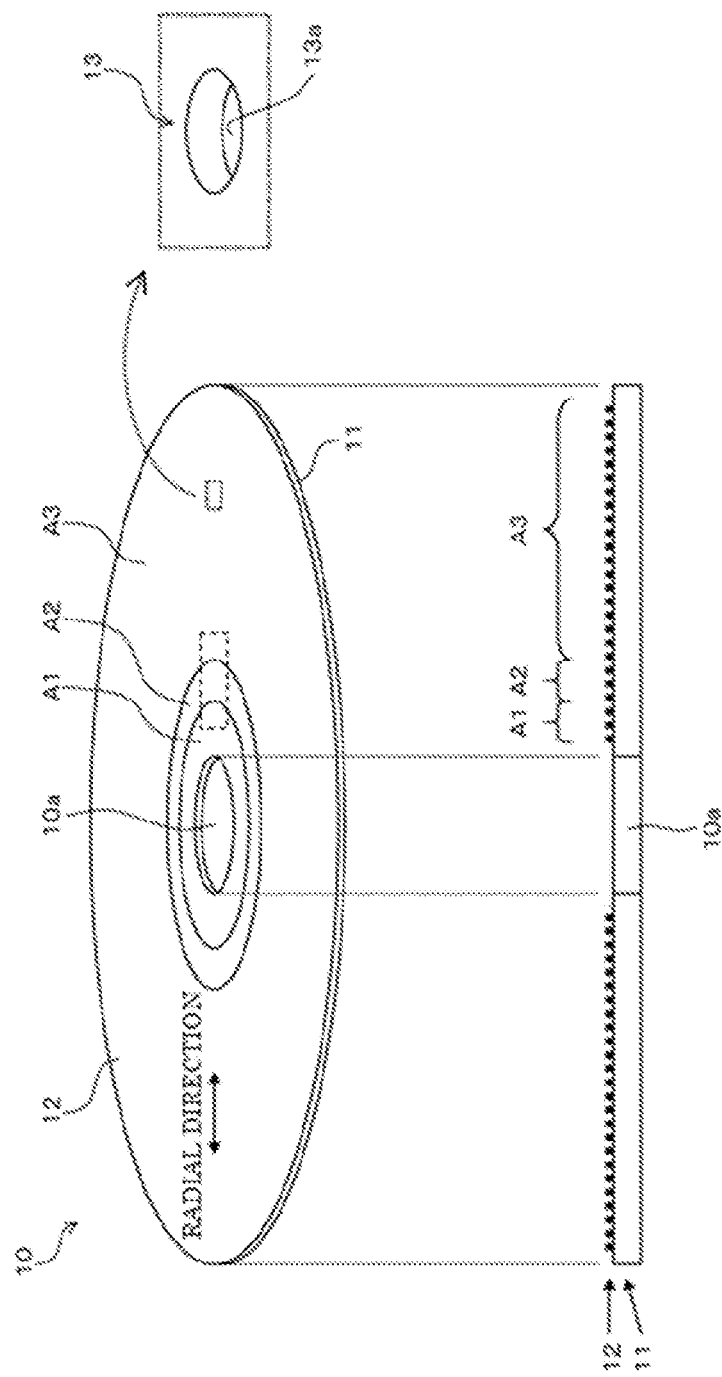
FIG. 1 is a schematic configuration of a biosensor substrate of a first embodiment.

FIG. 1 is a schematic configuration of biosensor substrate 10 of the present embodiment. Biosensor substrate 10 is used, for example, to detect erythrocytes infected with malaria parasites in human blood.

As shown in the perspective view of the upper part of FIG. 1, biosensor substrate 10 is disc-shaped like an optical disc (such as a CD or DVD), and has circular hole 10a at its center. Biosensor substrate 10 includes base substrate 11 and well layer 12 formed on the upper surface of base substrate 11.

As shown in the perspective view in the upper part and the sectional view in the lower part of FIG. 1, well layer 12 is divided into three regions: fluorescent region A1, non-fluorescent region A2, and well region A3 in this order from the center to the periphery. Each region is set before use as follows: fluorescent region A1 is previously coated with a fluorescent material (described later), whereas non-fluorescent region A2 is not. When biosensor substrate 10 is in use, samples are dropped in well region A3, but not in fluorescent region A1 or non-fluorescent region A2. Thus, when biosensor substrate 10 is in use, the samples are held in wells 13, and the fluorescence generated from the samples is detected.

Well region A3 contains a plurality of minuscule wells 13 each having a columnar hollow. Such well 13 is shown in the enlarged view on the extreme right of FIG. 1. Wells 13 are substantially concentrically arranged from the center of biosensor substrate 10 outward. Each well 13 has bottom surface portion 13a sunken below the top surface of well layer 12. Bottom surface portion 13a has a diameter and a height to hold a drop of each sample. Fluorescent region A1 and non-fluorescent region A2 do not have wells 13, and have spiral grooves 15, which will be described later with reference to FIG. 2A.

FIG. 2A is an enlarged view of the dotted-line rectangle shown in the perspective view of FIG. 1, and FIG. 2B is an enlarged view of the dotted-line rectangle shown in FIG. 2A.

As shown in FIG. 2B, the upper surface of base substrate 11 (the surface on the well layer 12 side) is provided with a spiral track as in an optical disc. The track is formed of meandering grooves, which store address information for locating positions on the surface of biosensor substrate 10. Similar to a CD or DVD, the address information is reproduced by scanning the track at constant linear velocity with excitation light (described later). The track is extended spirally from the innermost periphery to the outermost periphery of biosensor substrate 10. Reflective film 14 is provided between base substrate 11 and well layer 12. Reflecting surface 11a that is of an interface between reflecting film 14 and base substrate 11 is formed on the upper surface of base substrate 11 by stacking reflecting film 14 on the upper surface of base substrate 11.

Wells 13 are arranged at predetermined intervals on the upper surface of well region A3. Bottom surface portion 13a of each well 13 is slightly higher than reflective film 14 so as to be away from the upper surface of reflective film 14. Grooves 15 are formed spirally at predetermined intervals in the radial direction on the upper surface of fluorescent region A1 and non-fluorescent region A2. Between grooves 15 adjacent to each other in the radial direction, there are provided planar portions 16. Each groove 15 in fluorescent region A1 has fluorescent bottom surface portion 15a coated with a fluorescent material. Each groove 15 in non-fluorescent region A2 has non-fluorescent bottom surface portion 15b not coated with a fluorescent material. Fluorescent bottom surface portion 15a and non-fluorescent bottom surface portion 15b are slightly higher than reflective film 14 so as to be away from the upper surface of reflective film 14. Fluorescent bottom surface portion 15a, non-fluorescent bottom surface portion 15b, and bottom surface portion 13a of each well 13 are equidistant from the upper surface of reflective film 14. This aligns the positions to detect fluorescence in these regions, thereby improving the correlation between these regions.

Fluorescent region A1 is used to set a fluorescent signal gain factor G in order to amplify the fluorescence generated in the erythrocytes infected with malaria parasites to an appropriate level. Non-fluorescent region A2 is used to set a threshold Vsh in order to adequately detect the fluorescence generated in the erythrocytes infected with malaria parasites. The setting of the fluorescent signal gain factor G and the threshold Vsh will be described later with reference to FIGS. 8A to 8C. The arrangement of fluorescent region A1 in the inner portion of biosensor substrate 10 allows stable fluorescence detection in regions having small deformation such as surface wobbling or tilting. This reduces the error in detecting fluorescence caused by fluorescent region A1.

Each well 13 has a diameter d1 and a height d2. Bottom surface portion 13a and reflective surface 11a have a distance d3 between them. Wells 13 have a distance d4 between each other. Similarly, grooves 15 have a width d1' and a height d2'. Fluorescent bottom surface portion 15a and reflective surface 11a have a distance d3' between them. Non-fluorescent bottom surface portion 15b and reflective surface 11a also have the distance d3'. Grooves 15 have a distance d4' between each other. Base substrate 11 has a thickness d5, and reflective surface 11a has a track pitch d6. In the present embodiment, the dimensions d1 to d6 are set to 100 µm, 50 µm, 2 µm, 300 µm, 0.6 mm, and 1 µm, respectively. Furthermore, the dimensions d1' to d4' are set to 100 µm, 50 µm, 2 µm, and 300 µm, respectively, which are identical to the dimensions d1 to d4. Planar portions 16 and reflective surface 11a have a distance of (d2'+d3') between them. The reflectance of excitation light (described later) for reflective film 14 is set to 3 to 4%.

In the present embodiment, base substrate 11 is made of polycarbonate. Well layer 12 is made of ultraviolet curable resin. Reflective film 14 is made of metal such as aluminum or a silver alloy; a dielectric material such as niobium oxide; or a wavelength selection film. Base substrate 11 may alternatively be made, for example, of polymethyl methacrylate or amorphous polyolefin, besides polycarbonate. Well layer 12 may alternatively be made, for example, of silicone, polycarbonate, polymethyl methacrylate, amorphous polyolefin, or a transparent material such as a biodegradable material. Reflective film 14 is set to have a thickness of, for example, 5 nm to 20 nm so as to have a desired reflectance of the excitation light. It is also preferable that the material and thickness of reflective film 14 be set to have a high reflectance for the wavelength of the excitation light and a low reflectance for the wavelength of the fluorescence.

In the present embodiment, whether erythrocytes, which are the test objects, are infected with malaria parasites or not is examined using a fluorescent material as a fluorescent label, such as Pacific Blue, SYTO40, Cascade Yellow, or Fluolid-W Yellow. The fluorescent material used as the fluorescent label is configured to generate fluorescence when coming into contact with the nucleus of a malaria parasite under exposure to excitation light. It is preferable that the fluorescent material used in fluorescent bottom surface portion 15a could be an inorganic fluorescent material such as $BaMgAl_{10}O_{17}$:Eu, $Ba_2SiO_4$:Eu, ZnS:Cu, or Al. The reason for this is as follows. If a fluorescent material that reacts with a living body, such as Pacific Blue, SYTO40, Cascade Yellow, or Fluolid-W Yellow, is previously coated, the fluorescent material may be degraded with time or exposure to light. In contrast, an inorganic fluorescent material is not readily degraded and the degradation speed is very slow, making it easy to manage the period and method of storage. In the case, however, that the fluorescent material that reacts with a living body is not degraded or the degradation speed is manageable, the same fluorescent material as is used for the test object can be used in fluorescent bottom surface portion 15a instead of the inorganic material. The fluorescent material coated on fluorescent bottom surface portion 15a is configured to generate fluorescence having the same wavelength as the fluorescence generated in the nucleus of a malaria parasite by exposure to excitation light. The fluorescent material to be coated on fluorescent bottom surface portion 15a is selected in such a manner that the fluorescence generated from fluorescent bottom surface portion 15a has about the same intensity as the fluorescence generated from the nucleus of a malaria parasite. Coating the above-mentioned fluorescent material on fluorescent bottom surface portion 15a allows fluorescence detection from the same height as bottom surface portion 13a of each well 13, thereby improving the correlation of fluorescence intensity between the regions.

FIGS. 3A-3D show how to form biosensor substrate 10.

Figure 3A:
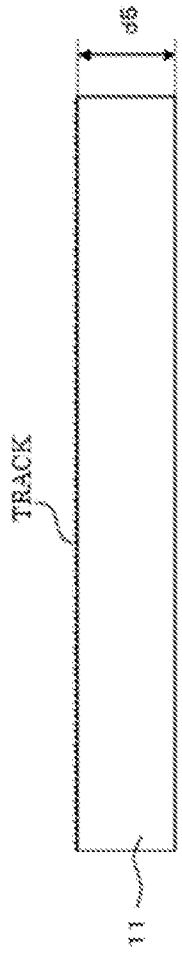
FIGS. 3A-3D show how to form the biosensor substrate of the first embodiment.
Figure 3B:
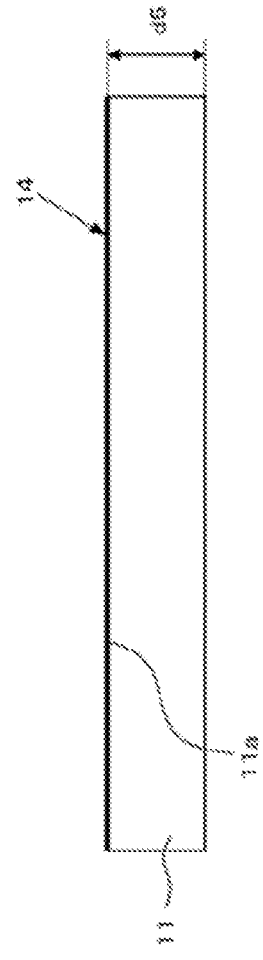
Figure 3C:
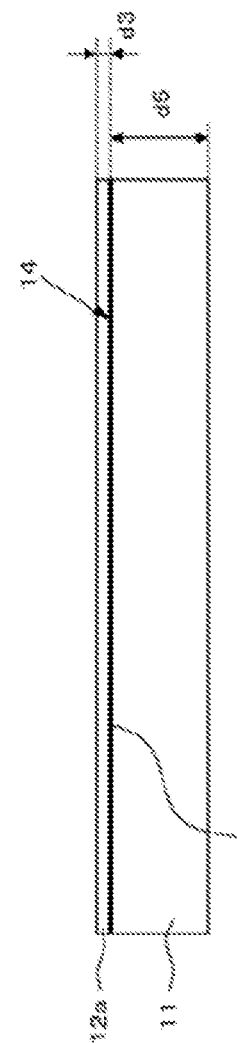
Figure 3D:
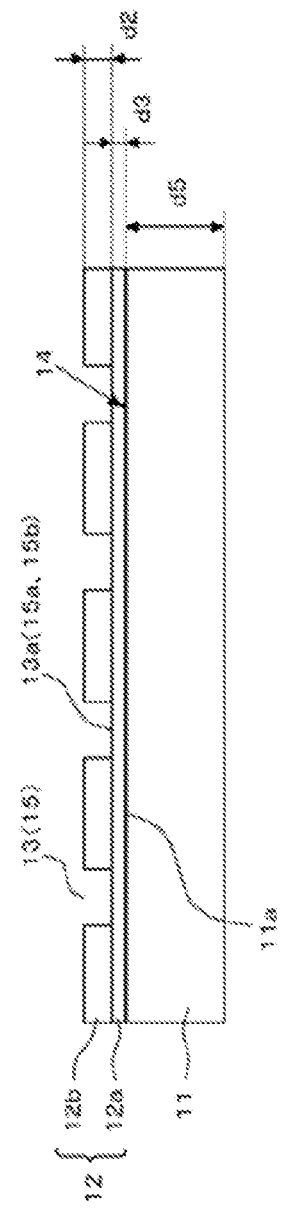

First, as shown in FIG. 3A, base substrate 11 is formed by injection molding. Base substrate 11 has a thickness d5, and is provided with a series of track portions on its upper surface. Next, as shown in FIG. 3B, reflective film 14 is formed on the upper surface of base substrate 11, so that reflective surface 11a is formed on the track portions on the upper surface of base substrate 11. Then, as shown in FIG. 3C, bottom surface layer 12a is spin-coated on the upper surface of reflective film 14. Next, as shown in FIG. 3D, top surface layer 12b having a thickness d2 is formed by 2P molding on the upper surface of bottom surface layer 12a. Consequently, a plurality of wells 13 and a plurality of grooves 15 are formed, and well layer 12 is formed of a combination of bottom surface layer 12a and top surface layer 12b. Then, a fluorescent material is coated on the bottom surface of grooves 15 in fluorescent region A1 so as to make it fluorescent bottom surface portion 15a.

In the case of forming top surface layer 12b by 2P molding on the upper surface of bottom surface layer 12a, it is necessary to arrange a stamper (well stamper) for 2P molding properly with respect to base substrate 11 so that the address information stored in the track can correspond to wells 13 and grooves 15.

Figure 4A:
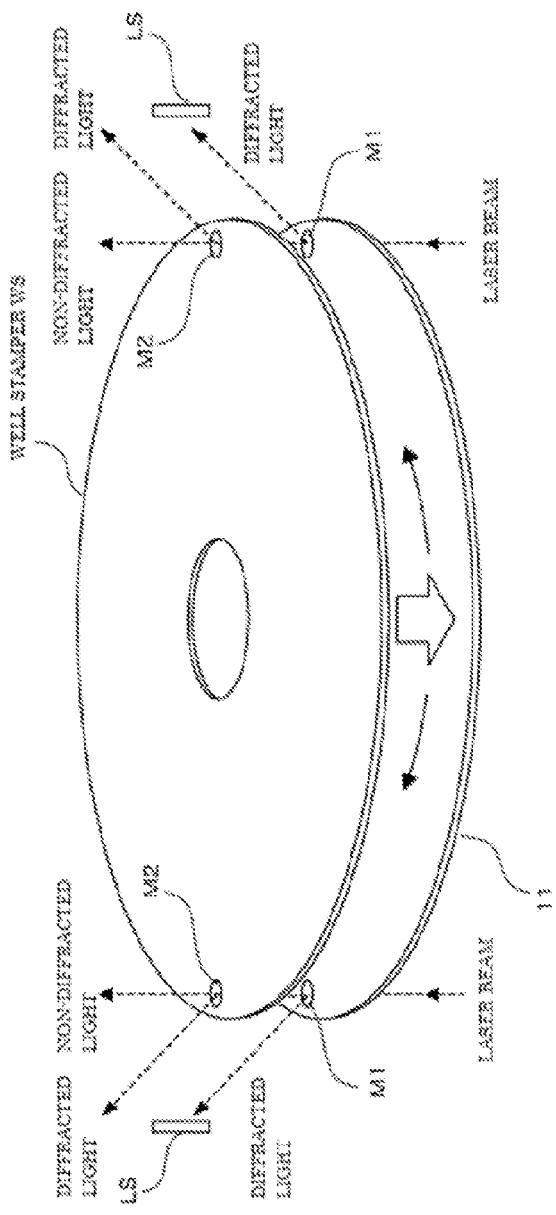
FIGS. 4A and 4B show how to position a well stamper relative to a base substrate in the first embodiment.
Figure 4B:
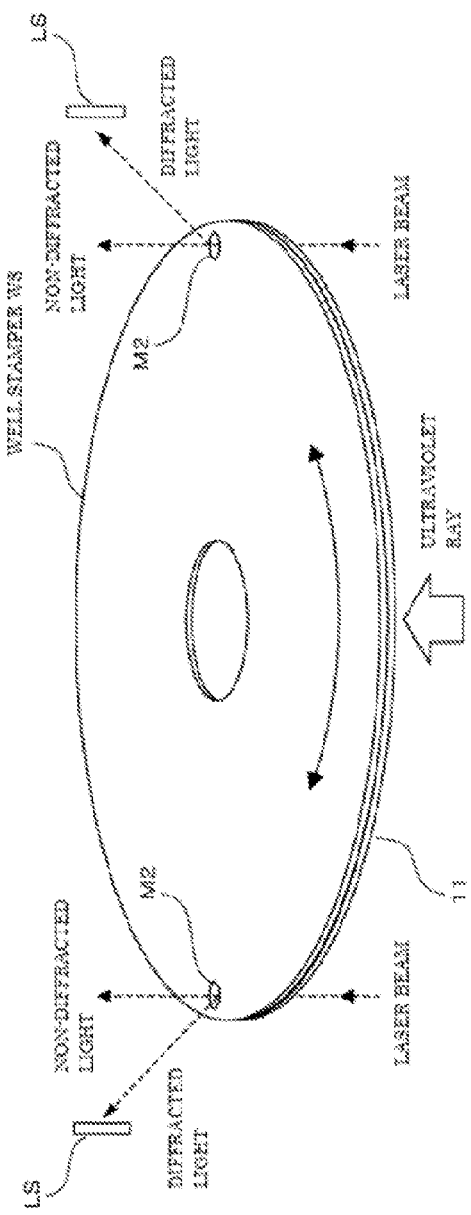

FIGS. 4A and 4B show how to position a well stamper WS relative to base substrate 11.

In this positioning method, base substrate 11 has two small diffraction areas M1 as positioning markers symmetrical with respect to the center of base substrate 11. These diffraction areas M1 are formed by forming a diffraction pattern in the outer peripheral region not having grooves on the upper surface of base substrate 11 when base substrate 11 is injection molded. The well stamper WS is provided with two small diffraction areas M2 as markers formed at positions corresponding to the diffraction areas M1. Furthermore, two laser light sources are disposed at positions where laser light is incident into each of the two diffraction areas M1 when base substrate 11 is in position. These laser light sources emit laser light upward. In addition, light sensors LS are disposed at positions where the laser light diffracted by the diffraction areas M1 and M2 (diffracted light) is received.

At the time of 2P molding, as shown in FIG. 4A, first, base substrate 11 is positioned in the circumferential direction so that the diffracted light generated by two diffraction areas M1 is received by the respective light sensors LS. At this moment, some parts of the laser light (zero-order diffracted light: non-diffracted light) are not diffracted by the diffraction areas M1, but pass through them. Next, the well stamper WS is approached to the upper surface of base substrate 11. At the same time, the well stamper WS is positioned in the circumferential direction so that the non-diffracted light which has passed through the diffraction areas M1 can be incident into the diffraction areas M2. In other words, the well stamper WS is positioned in the circumferential direction so that the diffracted light generated by the two diffraction areas M2 when the non-diffracted light is incident can be received by the respective light sensors LS. Thus, the well stamper WS is pushed against the upper surface of base substrate 11 with base substrate 11 and well stamper WS in position. In this situation, ultraviolet light is applied to cure the ultraviolet curable resin, so that top surface layer 12b is completed.

The positioning between base substrate 11 and the well stamper WS may alternatively be performed by other methods than described above. For example, a projection and a recess may be formed in the well stamper WS and base substrate 11, respectively, and they may be fitted into each other.

Figure 5:
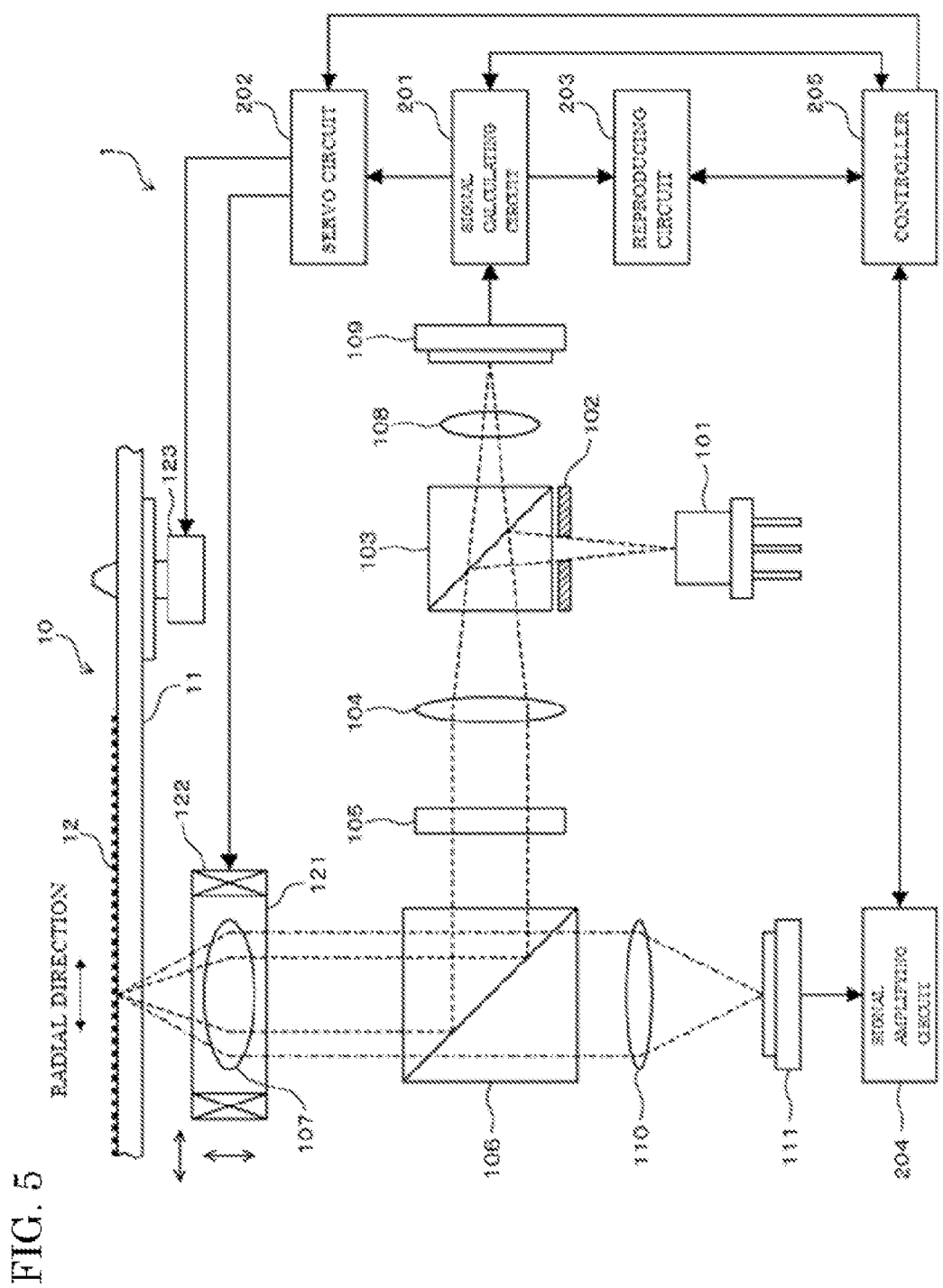
FIG. 5 is a configuration of a fluorescence detection device of the first embodiment.

FIG. 5 is a configuration of fluorescence detection device 1 of the present embodiment. Fluorescence detection device 1 is used, for example, to determine whether the erythrocytes held in wells 13 of biosensor substrate 10 are infected with malaria parasites or not.

Samples are prepared by fluorescently-labeled test objects prior to the use of fluorescence detection device 1 and are placed into wells 13 of biosensor substrate 10. The test objects used in the present embodiment are erythrocytes approximately 10 µm in diameter and approximately 2 µm in thickness. The erythrocytes, which may or may not be infected with malaria parasites are parallel-arranged on bottom surface portion 13a of each well 13, which is 100 µm in diameter. The nuclei of infected erythrocytes will be fluorescently-labeled. Biosensor substrate 10 with the samples held thereon is set on rotation device 123 (turntable) of fluorescence detection device 1 by aligning hole 10a (see FIG. 1) with the center of rotation device 123. Then, the measurement is started.

The optical system of fluorescence detection device 1 includes semiconductor laser 101, aperture 102, polarizing beam splitter (PBS) 103, collimator lens 104, quarter wavelength plate 105, dichroic prism 106, object lens 107, anamorphic lens 108, light detector 109, condenser lens 110, and fluorescence detector 111. Besides the optical system, fluorescence detection device 1 further includes holder 121, object lens actuator 122, rotation device 123, signal calculating circuit 201, servo circuit 202, reproducing circuit 203, signal amplifying circuit 204, and controller 205.

The optical system, holder 121, and object lens actuator 122 of fluorescence detection device 1 are accommodated in a housing like an existing optical pickup device used for recording and reproduction in a CD or DVD. The housing can be moved in the radial direction of biosensor substrate 10 by a predetermined guide mechanism. Servo circuit 202 also controls the movement of this housing. This control is an access control similar to that used in an existing CD or DVD player; therefore, a detailed description thereof will be omitted.

Semiconductor laser 101 emits laser light (hereinafter, the excitation light) with a wavelength of approximately 405 nm. The excitation light referred to in the present embodiment is one example of the irradiation light described in the claims. In FIG. 5, a part of the excitation light emitted by semiconductor laser 101 passes through aperture 102 and is guided to biosensor substrate 10, the excitation light is shown by dotted lines. Aperture 102 has a circular opening with a predetermined diameter so as to limit the diameter of the excitation light. Semiconductor laser 101 is positioned so that the excitation light emitted from semiconductor laser 101 can be s-polarized with respect to PBS 103. As a result, the excitation light emitted from semiconductor laser 101 is reduced in diameter by aperture 102, then is reflected by PBS 103, and is incident on collimator lens 104.

Collimator lens 104 converts the excitation light incident from PBS 103 into parallel light having a predetermined diameter. Quarter wavelength plate 105 converts the excitation light incident from collimator lens 104 into circularly polarized light. Quarter wavelength plate 105 also converts the excitation light incident from dichroic prism 106 into linearly polarized light, which is at right angles to the direction in which the excitation light incident from collimator lens 104 is polarized. As a result, the excitation light incident on PBS 103 from collimator lens 104 passes through PBS 103.

Dichroic prism 106 is configured to reflect laser light with a wavelength of approximately 405 nm and to transmit laser light with a wavelength of approximately 450 to 540 nm. Therefore, the excitation light incident from quarter wavelength plate 105 is reflected by dichroic prism 106 and then is incident on object lens 107.

Object lens 107 is configured to converge excitation light on biosensor substrate 10 properly. More specifically, object lens 107 is configured to converge the excitation light incident from dichroic prism 106 with a predetermined numerical aperture (NA), which is 0.34 in this case. The diameter of the excitation light incident on object lens 107 is determined by the diameter of aperture 102. The focal depth of the excitation light converged by object lens 107 is determined by the NA of the excitation light. The focal depth of the excitation light will be described later with reference to FIGS. 7A and 7B.

Object lens 107, which is held in holder 121, is driven by object lens actuator 122 in the focusing direction (the direction perpendicular to biosensor substrate 10) and the tracking direction (the radial direction of biosensor substrate 10). In short, object lens 107 is driven to follow the track formed of the grooves while the excitation light is focused on reflective surface 11a of biosensor substrate 10. Some of the excitation light focused on reflective surface 11a is reflected by reflective surface 11a, but the most of it passes through reflective surface 11a.

The excitation light reflected by reflective surface 11a (hereinafter, reflected excitation light) is reflected by dichroic prism 106, converted into linearly polarized light by quarter wavelength plate 105, and made into convergent light by collimator lens 104. The reflected excitation light incident on PBS 103 from collimator lens 104 passes through PBS 103 as described above.

Anamorphic lens 108 introduces astigmatism to the reflected excitation light which is incident from PBS 103. The reflected excitation light that has passed through anamorphic lens 108 is incident on light detector 109. Light detector 109 includes a four-quadrant sensor for receiving the reflected excitation light on its light-receiving surfaces. The detection signals of light detector 109 are entered to signal calculating circuit 201.

On the other hand, when the excitation light converged by object lens 107 scans the positions corresponding to wells 13, of the excitation light applied to biosensor substrate 10, the part that has passed through reflective surface 11a reaches bottom surface portions 13a of wells 13. When the excitation light is applied to the erythrocytes fluorescently-labeled and parallel-arranged on bottom surface portion 13a, the erythrocytes infected with malaria parasites fluoresce. This fluorescence shown by chain lines in FIG. 5 has a larger numerical aperture (NA) than the excitation light. Therefore, between object lens 107 and dichroic prism 106, the fluorescent light has a larger beam diameter than the excitation light. The NA of the fluorescent light is, for example, 0.65. Furthermore, the fluorescence has a wavelength of 450 to 540 nm in the present embodiment, which is different from that of the excitation light. In contrast, fluorescence is not generated in the erythrocytes uninfected with malaria parasites because they are not fluorescently-labeled. Thus, erythrocytes infected with malaria parasites and those uninfected can be distinguished.

When the excitation light converged by object lens 107 scans the positions corresponding to grooves 15 in fluorescent region A1 or non-fluorescent region A2, of the excitation light applied to biosensor substrate 10, the part that has passed through reflective surface 11a reaches fluorescent bottom surface portion 15a or non-fluorescent bottom surface portion 15b. When the excitation light is applied to fluorescent bottom surface portion 15a, fluorescence is generated in the fluorescent material coated on fluorescent bottom surface portion 15a. The wavelength of the fluorescence is 450 to 540 nm, which is the same as that of the fluorescence generated in the above-mentioned malaria parasites. In FIG. 5, the fluorescence generated in the fluorescent material is shown by chain lines in the same manner as the fluorescence generated in the malaria parasites.

The fluorescence incident on dichroic prism 106 from object lens 107 passes through dichroic prism 106. The fluorescence incident from dichroic prism 106 is collected by condenser lens 110, which leads the fluorescence to fluorescence detector 111. Fluorescence detector 111 includes a sensor for receiving fluorescence on its light-receiving surfaces. The detection signals of fluorescence detector 111 are entered to signal amplifying circuit 204.

Signal calculating circuit 201 generates a focus error signal FE and a tracking error signal TE (both described later) from the detection signals of light detector 109. Signal calculating circuit 201 also generates wobble signals corresponding to the meandering shape of the track (grooves) from the detection signals of light detector 109. Servo circuit 202 controls the driving of object lens actuator 122 using the focus error signal FE and the tracking error signal TE sent from signal calculating circuit 201. Servo circuit 202 also controls rotation device 123 using the wobble signals sent from signal calculating circuit 201 so that biosensor substrate 10 can be rotated at constant linear velocity. Reproducing circuit 203 demodulates the wobble signals sent from signal calculating circuit 201, and generates reproduction data.

Signal amplifying circuit 204 amplifies the detection signals of fluorescence detector 111 on the basis of the fluorescent signal gain factor G, and outputs the amplified signals to controller 205. The fluorescent signal gain factor G of signal amplifying circuit 204 is set by controller 205 as will be described later.

Controller 205 controls signal calculating circuit 201, servo circuit 202, reproducing circuit 203, and other units of fluorescence detection device 1. Controller 205 detects the fluorescence generated in well region A3 and fluorescent region A1 on the basis of the output signal of signal amplifying circuit 204. Controller 205 then determines the positions where fluorescence is generated, on the basis of the detected fluorescence and the reproduction data (address information) sent from reproducing circuit 203. Controller 205 also stores, in its internal memory, the address information corresponding to the positions in well region A3 where the fluorescence is generated.

Furthermore, controller 205 sets the fluorescent signal gain factor G of signal amplifying circuit 204 on the basis of the output signal of signal amplifying circuit 204. Controller 205 also sets the threshold Vsh for extracting a signal corresponding to the fluorescence generated in the malaria parasites from the signals received from signal amplifying circuit 204.

Figure 6:
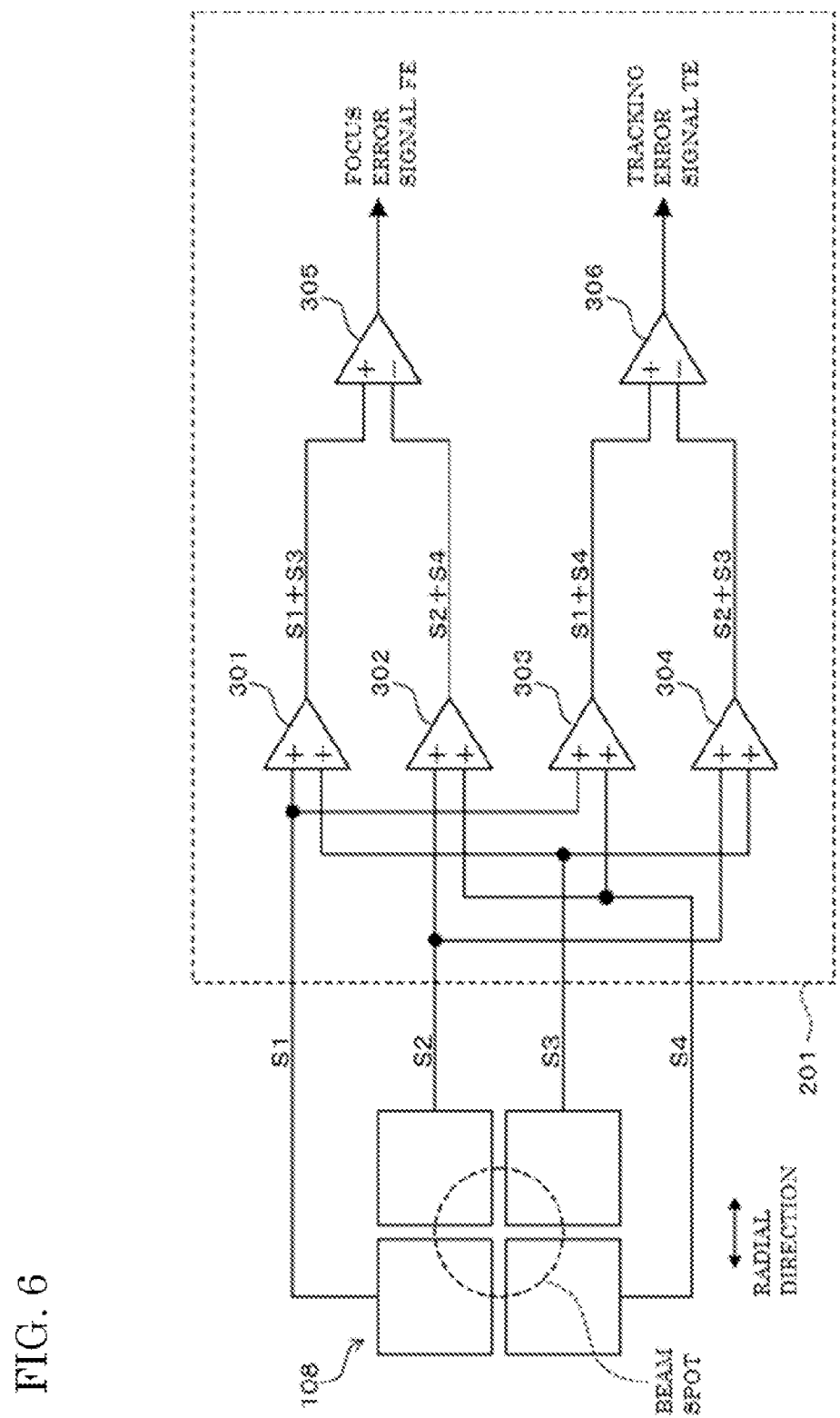
FIG. 6 is a circuit configuration of a signal calculating circuit in the first embodiment.

FIG. 6 is a circuit configuration of signal calculating circuit 201.

Light detector 109 includes a four-quandrant sensor for receiving the reflected excitation light on its light-receiving surfaces as described above. The four-quandrant sensor is configured to output detection signals S1-S4 on the basis of the beam spot of the reflected excitation light received on the upper left-, upper right-, lower right-, and lower left-hand light-receiving surfaces, respectively. In FIG. 6, the horizontal direction of the light-receiving surfaces of light detector 109 corresponds to the radial direction of the disc. The focus error signal FE and the tracking error signal TE are generated by the astigmatism method and the one-beam push-pull method, which are used in existing optical disc devices.

Signal calculating circuit 201 includes adders 301-304, and subtractors 305 and 306. Adder 301 outputs the sum of detection signals S1 and S3 to subtractor 305. Adder 302 outputs the sum of detection signals S2 and S4 to subtractor 305. Adder 303 outputs the sum of detection signals S1 and S4 to subtractor 306. Adder 304 outputs the sum of detection signals S2 and S3 to subtractor 306.

Subtractor 305 subtracts the output signals of adders 301 and 302, and outputs the focus error signal FE. Subtractor 306 subtracts the output signals of adders 303 and 304, and outputs the tracking error signal TE. Thus, the focus error signal FE and the tracking error signal TE are calculated by the following Formulas (1) and (2), respectively.

$$FE = (S1 + S3) - (S2 + S4) \quad (1)$$

$$TE = (S1 + S4) - (S2 + S3) \quad (2)$$

When the focal position of object lens 107 is located on reflective surface 11a, the beam spot on the four-quandrant sensor of light detector 109 becomes a circle of least confusion, and the focus error signal FE in Formula (1) has a value of 0. When the focal position of object lens 107 is just above the track portions (grooves) of reflective surface 11a, the beam spot on the four-quandrant sensor of light detector 109 falls equally between the two left-hand sensors and the two right-hand sensors, and the tracking error signal TE in Formula (2) has a value of 0.

The waveform signals (wobble signals) corresponding to the meandering shape of the track (grooves) are acquired on the basis of the tracking error signal TE. More specifically, the wobble signals are acquired by extracting the frequency components corresponding to the wobble signals from the tracking error signal TE. The wobble signals are generated by the technique used, for example, in existing DVD players.

Figure 7A:
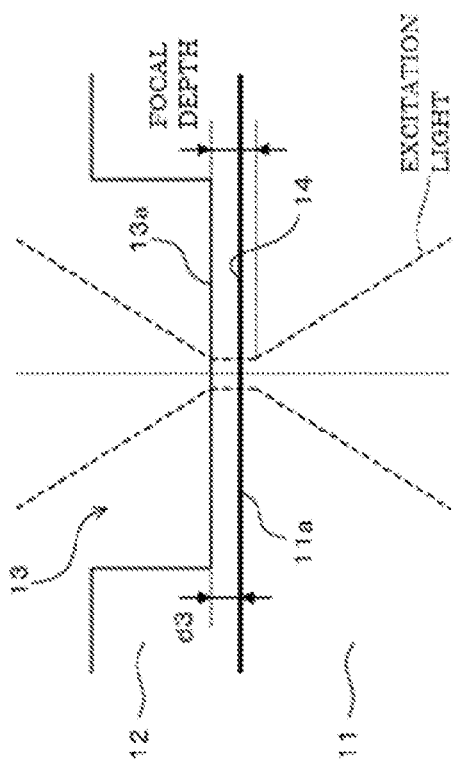
FIGS. 7A and 7B are explanatory diagrams of the focal depth of excitation light in the first embodiment.
Figure 7B:
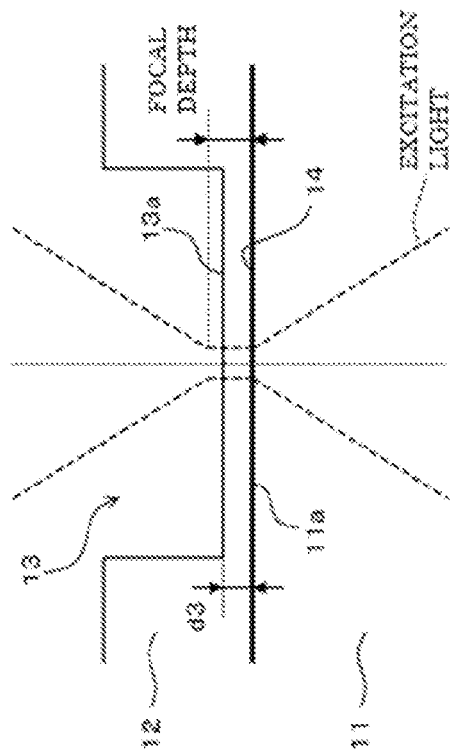

FIGS. 7A and 7B are explanatory diagrams of the focal depth of the excitation light.

As mentioned above, the excitation light has a wavelength of 405 nm and a numerical aperture (NA) of 0.34. In general, the focal depth can be calculated by the following formula: wavelength/(NA×NA). Therefore, the focal depth of the excitation light in the present embodiment is approximately 3.5 µm. The distance d3 between bottom surface portion 13a and reflective surface 11a shown in FIGS. 2A and 2B is set smaller than the focal depth of the excitation light, which is 2.0 µm in this case.

When the NA of the excitation light is set as above, the spot diameter at the focal position is approximately 1 µm. The track pitch d6 shown in FIG. 2B is set to 1 µm, which is substantially identical to the spot diameter. The nuclei of the malaria parasites each form a fluorescent spot of approximately 1 µm due to exposure to the excitation light. As a result, the excitation light spot can converge to the size of the nuclei of the malaria parasites, allowing the samples to be closely scanned with the excitation light spot, thereby ensuring the detection of the nucleus of the malaria parasites.

FIG. 7A shows the case in which the lowest point in the range of the focal depth of the excitation light coincides with the position of reflective film 14. FIG. 7B shows the case in which the highest point in the range of the focal depth of the excitation light coincides with the position of bottom surface portion 13a. Adjusting the offset voltage sent from servo circuit 202 to object lens actuator 122 can shift the focal depth of the excitation light to the back side (in the upward direction in FIG. 7A) or to somewhere in the range between FIGS. 7A and 7B from the position shown in FIG. 7A.

In the cases shown in FIGS. 7A and 7B, the distance d3 between bottom surface portion 13a of each well 13 and reflective surface 11a is 2 µm, and the focal depth of the excitation light is 3.5 µm. Consequently, both bottom surface portion 13a and reflective surface 11a are included in the range corresponding to the focal depth of the excitation light. Therefore, if the focal position of the excitation light is located on reflective surface 11a by focus servo control, the samples held on bottom surface portion 13a are also focused. Similar to the case of bottom surface portion 13a, when the excitation light is focused on reflective surface 11a in fluorescent bottom surface portion 15a, fluorescent bottom surface portion 15a is contained in the range of the focal depth of the excitation light. When the excitation light is focused on reflective surface 11a in non-fluorescent bottom surface portion 15b, non-fluorescent bottom surface portion 15b is contained in the range of the focal depth.

Figure 8A:
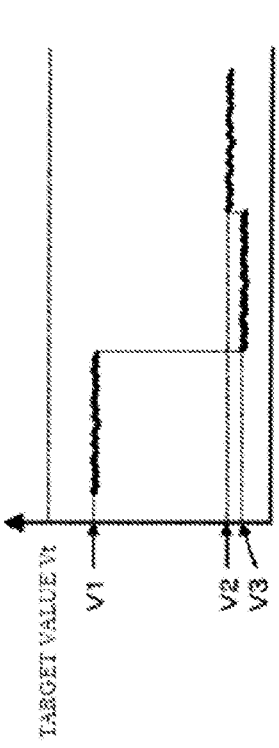
FIG. 8A is a flowchart showing how the controller sets a fluorescent signal gain factor and a threshold.

FIG. 8A is a flowchart showing how controller 205 sets the fluorescent signal gain factor G and the threshold Vsh. Before the execution of the flowchart shown in FIG. 8A, controller 205 sets a default value of the fluorescent signal gain factor G in signal amplifying circuit 204 shown in FIG. 5.

First, controller 205 moves the focal position of object lens 107 to fluorescent region A1, and drives object lens actuator 122 so as to focus the excitation light on reflective surface 11a in fluorescent region A1 (S11). The focal position is moved to fluorescent region A1 by, for example, the address searching which is used in existing CD or DVD players. When focused on reflective surface 11a of fluorescent region A1 in this manner, the excitation light is also focused on fluorescent bottom surface portion 15a of fluorescent region A1 as described with reference to FIGS. 7A and 7B. When the excitation light is applied to fluorescent bottom surface portion 15a, the fluorescence generated in fluorescent bottom surface portion 15a is incident on fluorescence detector 111.

Next, controller 205 acquires a maximum value V1 of the detection signals of fluorescence detector 111 corresponding to the fluorescence generated in fluorescent bottom surface portion 15a (S12). More specifically, controller 205 acquires the detection signals corresponding to fluorescent bottom surface portion 15a shown in FIG. 8B via signal amplifying circuit 204, and determines the maximum value of the acquired detection signals to be V1.

Figure 8B:
FIG. 8B shows detection signals of a fluorescence detector.

In this situation, if the focal position of object lens 107 is moved to the position corresponding to planar portions 16 either in fluorescent region A1 or in non-fluorescent region A2, the detection signals of fluorescence detector 111 have a maximum value V2 as shown in FIG. 8B. If the focal position of object lens 107 is moved to the position corresponding to non-fluorescent bottom surface portion 15b in non-fluorescent region A2, the detection signals of fluorescence detector 111 have a maximum value V3 as shown in FIG. 8B. Thus, even when the focal position is moved to the positions corresponding to planar portions 16 and non-fluorescent bottom surface portion 15b, the detection signals of fluorescence detector 111 can be output, but have a very small level because of the noise such as dark current.

Figure 8C:
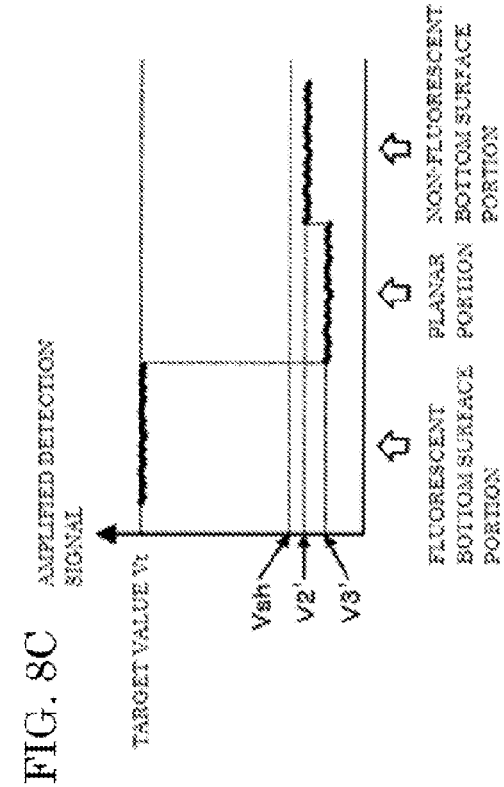
FIG. 8C shows amplified detection signals of the fluorescence detector in the first embodiment.

Next, controller 205 calculates a fluorescent signal gain factor G (=Vt/V1) to amplify the acquired maximum value V1 to a predetermined target value Vt (S13). Controller 205 then sets the calculated fluorescent signal gain factor G in signal amplifying circuit 204 (S14). As a result, as shown in FIG. 8C, the maximum value of the detection signals of fluorescent bottom surface portion 15a is set to the target value Vt.

Next, controller 205 moves the focal position of object lens 107 to non-fluorescent region A2 so as to focus the excitation light on reflective surface 11a of non-fluorescent region A2 (S15). As a result, in the same manner as in S11, the excitation light is focused also on non-fluorescent bottom surface portion 15b. At this moment, as shown in FIG. 8C, the output signal of signal amplifying circuit 204 has a maximum value V2', which is the product of the maximum value V2 and the fluorescent signal gain factor G. Controller 205 then acquires the maximum value V2' (S16). In this situation, if the focal position of object lens 107 is moved to the position corresponding to planar portions 16, as shown in FIG. 8C, the output signal of signal amplifying circuit 204 has a maximum value V3', which is the product of the maximum value V3 and the fluorescent signal gain factor G.

As described above, the height of fluorescent bottom surface portion 15a is set so that the fluorescence generated in fluorescent bottom surface portion 15a has about the same intensity as the fluorescence generated in the malaria parasites. Therefore, when the fluorescent signal gain factor G is set as above, the output signal of signal amplifying circuit 204 is set around the target value Vt in the case that the focal position of object lens 107 is located on the nuclei of the malaria parasites in wells 13. In contrast, when the focal position of object lens 107 is located on the samples not containing malaria parasites in wells 13, the output signal of signal amplifying circuit 204 is set around the maximum value V2'. When the focal position of object lens 107 is located on an area in well region A3 not containing wells 13, the output signal of signal amplifying circuit 204 is set around the maximum value V3'.

Next, controller 205 determines the threshold Vsh on the basis of the target value Vt and the maximum value V2' (S17). The threshold Vsh is larger than the maximum value V2' by a predetermined amount and is smaller than the target value Vt (S18). Consequently, of the amplified detection signals of fluorescence detector 111 shown in FIG. 8C, only values not less than the threshold Vsh, that is, the amplified detection signals corresponding to fluorescent bottom surface portion 15a are detected by controller 205.

When the detection signals which are output from fluorescence detector 111 in planar portions 16 and non-fluorescent bottom surface portion 15b are circuit noise such as dark current as described above, the magnitude of this detection signals is somewhat fixed. In contrast, the detection signals which are output from fluorescence detector 111 in fluorescent bottom surface portion 15a can change greatly depending on the causes in biosensor substrate 10 such as the degradation of the fluorescent material or the warpage of biosensor substrate 10. Consequently, in FIG. 8B, it may happen that the level of the detection signals which are output from fluorescence detector 111 in planar portions 16 and non-fluorescent bottom surface portion 15b is close to that of the detection signals which are output from fluorescence detector 111 in fluorescent bottom surface portion 15a. In such a case, if the fluorescent signal gain factor G is set on the basis of the maximum value V1 in S13, the detection signals (noise) output from fluorescence detector 111 in planar portions 16 and non-fluorescent bottom surface portion 15b are also greatly amplified. In this case, too, however, the threshold Vsh is set between the target value Vt and the amplified maximum value V2' in S17, so that the threshold Vsh is not less than the maximum value V2'. As a result, in this case, too, the fluorescence generated in the malaria parasites can be detected adequately. Thus, in the flowchart shown in FIG. 8A, the threshold Vsh is not fixed but is dynamically set depending on the amplified maximum value V2'. This allows the threshold Vsh to be dependent on the condition of biosensor substrate 10, and the fluorescence generated in the malaria parasites to be detected adequately.

In S17, the threshold Vsh is set depending on the maximum value V2' of the detection signals corresponding to non-fluorescent bottom surface portion 15b. Alternatively, the threshold Vsh may be set smaller than the target value Vt and larger by a predetermined amount than the larger of the two maximum values: the maximum value V2' of the detection signals corresponding to non-fluorescent bottom surface portion 15b and the maximum value V3' of the detection signals corresponding to planar portions 16.

As described above, in the present embodiment, biosensor substrate 10 includes not only wells 13 for holding samples, but also fluorescent bottom surface portion 15a which generates fluorescence in the same manner as the erythrocytes infected with malaria parasites. As a result, as shown in FIG. 8A, when the fluorescent signal gain factor G is set in fluorescence detection device 1, the maximum value of the detection signals of fluorescence detector 111 corresponding to the erythrocytes infected with malaria parasites can be amplified to near the target value Vt. This ensures the detection of the fluorescence generated in the malaria parasites.

In the case that the optical system is set differently in different fluorescence detection devices 1, the magnitude of the detection signals of fluorescence detector 111 corresponding to the erythrocytes infected with malaria parasites is also different from device to device. In this case, if the detection signals of the fluorescence generated in the malaria parasites are small, the fluorescence may not be detected.

In the present embodiment, however, biosensor substrate 10 includes fluorescent bottom surface portion 15a which certainly generates fluorescence. Therefore, fluorescence detection device 1 can figure out the signal level of the fluorescence to be detected from biosensor substrate 10 by applying the excitation light to fluorescent bottom surface portion 15a. More specifically, it is possible to figure out previously that if the detection signals of the fluorescence generated when the excitation light is applied to fluorescent bottom surface portion 15a are small, the signals of the fluorescence generated in the malaria parasites are also small. Then, in fluorescence detection device 1, the fluorescent signal gain factor G of signal amplifying circuit 204 is set so that the magnitude of the detection signals reaches an appropriate level. As a result, the maximum value of the detection signals of fluorescence detector 111 corresponding to the malaria parasites can be amplified to the target value Vt, which is appropriate for detection. The present embodiment has described that calibration is performed by adjusting the amplification after fluorescence detection, but may alternatively be performed by adjusting the intensity of the excitation light. In other words, the target value Vt appropriate for detection may be achieved by increasing the intensity of the excitation light, thereby increasing the amount of fluorescent signals. In this case, however, it is necessary to make sure that the fluorescent material and the samples are not degraded by the excitation light. By achieving this condition, even if the detection signals of the fluorescence generated in the malaria parasites are small because of the setting of the optical system or the condition of biosensor substrate 10, the fluorescence is less likely to escape detection. This results in an improvement in the accuracy of determining whether the erythrocytes are infected with malaria parasites or not. Furthermore, in the present embodiment, biosensor substrate 10 includes not only wells 13 for holding samples, but also fluorescent bottom surface portion 15a which generates fluorescence with nearly the same intensity as the fluorescence generated in the erythrocytes infected with malaria parasites. Alternatively, the fluorescence intensity of fluorescent bottom surface portion 15a may be higher by a fixed amount. The higher intensity allows easier detection in the fluorescence detector. In this case, the intensity of the signal detected in fluorescent bottom surface portion 15a is fixed relative to the intensity obtained from the erythrocytes infected with malaria parasites, and the intensity of the detection signals of fluorescence detector 111 corresponding to the malaria parasites is set. Thus, the intensity of the fluorescence generated in the malaria parasites can be set at a predetermined level or more by setting the fluorescent signal gain G at a fixed intensity in fluorescent bottom surface portion 15a.

In the present embodiment, fluorescent bottom surface portion 15a of grooves 15 and bottom surface portions 13a of wells 13 are nearly equidistant from reflective surface 11a. This allows the excitation light to be applied under the same irradiation conditions to both fluorescent bottom surface portion 15a and bottom surface portion 13a. As a result, the intensity of the fluorescence generated when wells 13 are exposed to the excitation light can be accurately figured out on the basis of the intensity of the fluorescence generated when fluorescent bottom surface portion 15a is exposed to the excitation light. As a result, in fluorescence detection device 1, the detection signals of the fluorescence generated when wells 13 are exposed to the excitation light can be more easily adjusted to an appropriate level.

In the present embodiment, fluorescent bottom surface portion 15a is coated with a fluorescent material having nearly the same intensity as the fluorescence generated in the samples by exposure to the excitation light. Consequently, the fluorescence generated when fluorescent bottom surface portion 15a is exposed to the excitation light has nearly the same intensity as the fluorescence generated in the samples held in wells 13. As a result, in fluorescence detection device 1, the detection signals of the fluorescence generated when wells 13 are exposed to the excitation light can be more easily adjusted to an appropriate level. If such a fluorescent material with nearly the same intensity as the fluorescence generated in the samples is not available to the fluorescent bottom surface portion 15a, it is possible to use a fluorescent material whose intensity is higher than that of the fluorescence generated in the samples and to adjust the concentration and impurities of the fluorescent material until reaching nearly the same fluorescence intensity.

In the present embodiment, non-fluorescent bottom surface portion 15b of grooves 15 and bottom surface portions 13a of wells 13 are nearly equidistant from reflective surface 11a. This allows the excitation light to be applied under the same irradiation conditions to both non-fluorescent bottom surface portion 15b and bottom surface portion 13a. As a result, the detection signals which are output from fluorescence detector 111 when non-fluorescent bottom surface portion 15b is exposed to the excitation light can be acquired as noise. Setting the threshold for detecting the fluorescence from the samples to a level exceeding that of these detection signals allows accurate detection of the fluorescence generated in the samples. Thus, the threshold Vsh is dynamically set in fluorescence detection device 1 as shown in FIG. 8C, thereby allowing adequate detection of the detection signals of fluorescence detector 111 corresponding to the erythrocytes infected with malaria parasites. This improves the detection accuracy of the fluorescence generated in the erythrocytes infected with malaria parasites.

<Second Embodiment>

Figure 9:
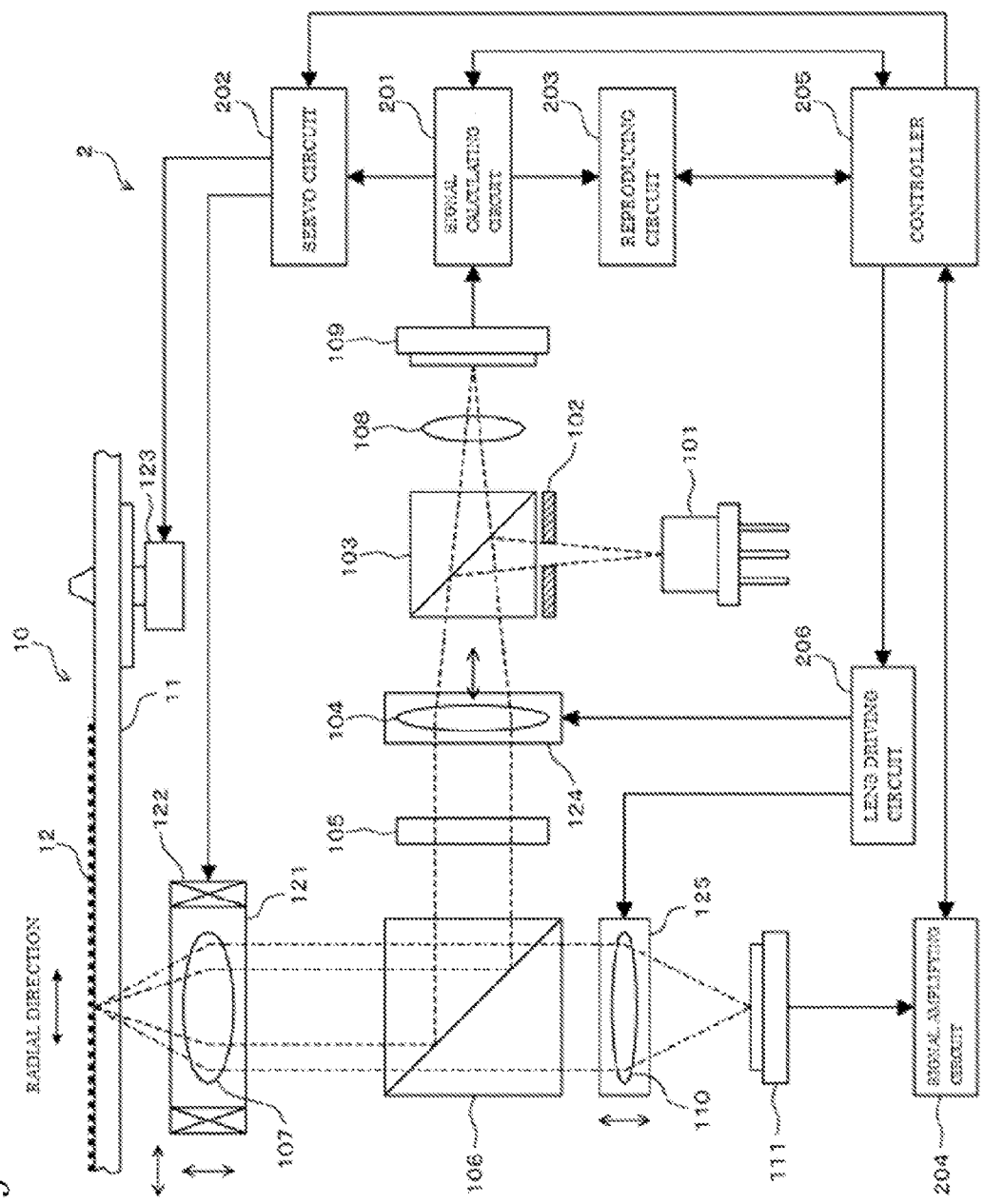
FIG. 9 is a configuration of a fluorescence detection device of a second embodiment.

FIG. 9 is a configuration of fluorescence detection device 2 of the present embodiment.

Fluorescence detection device 2 differs from fluorescence detection device 1 shown in FIG. 5 in having additional components: lens actuator 124 for moving collimator lens 104 along the optical axis of the excitation light; lens actuator 125 for moving the condenser lens 110 along the optical axis of the fluorescence; and lens driving circuit 206 for moving lens actuators 124 and 125. Lens actuators 124 and 125 are driven by controller 205 via lens driving circuit 206.

As in the first embodiment, the optical system of the present embodiment is configured as follows. When collimator lens 104 converts the excitation light into parallel light, the excitation light is focused on a prescribed position by object lens 107. The excitation light reflected from the focal position forms a circular (a circle of least confusion) beam spot on the light-receiving surfaces of light detector 109. The optical system allows collimator lens 104 to be moved along the optical axis while the focus servo control is on. This can shift the focal position of the beam that has passed through object lens 107 along the optical axis. As a result, the focal position of the excitation light on biosensor substrate 10 can be changed in the depth direction. The optical system also allows condenser lens 110 to be moved along the optical axis. This can change the position in the depth direction of the fluorescence on biosensor substrate 10, which is collected to fluorescence detector 111.

Figure 10:
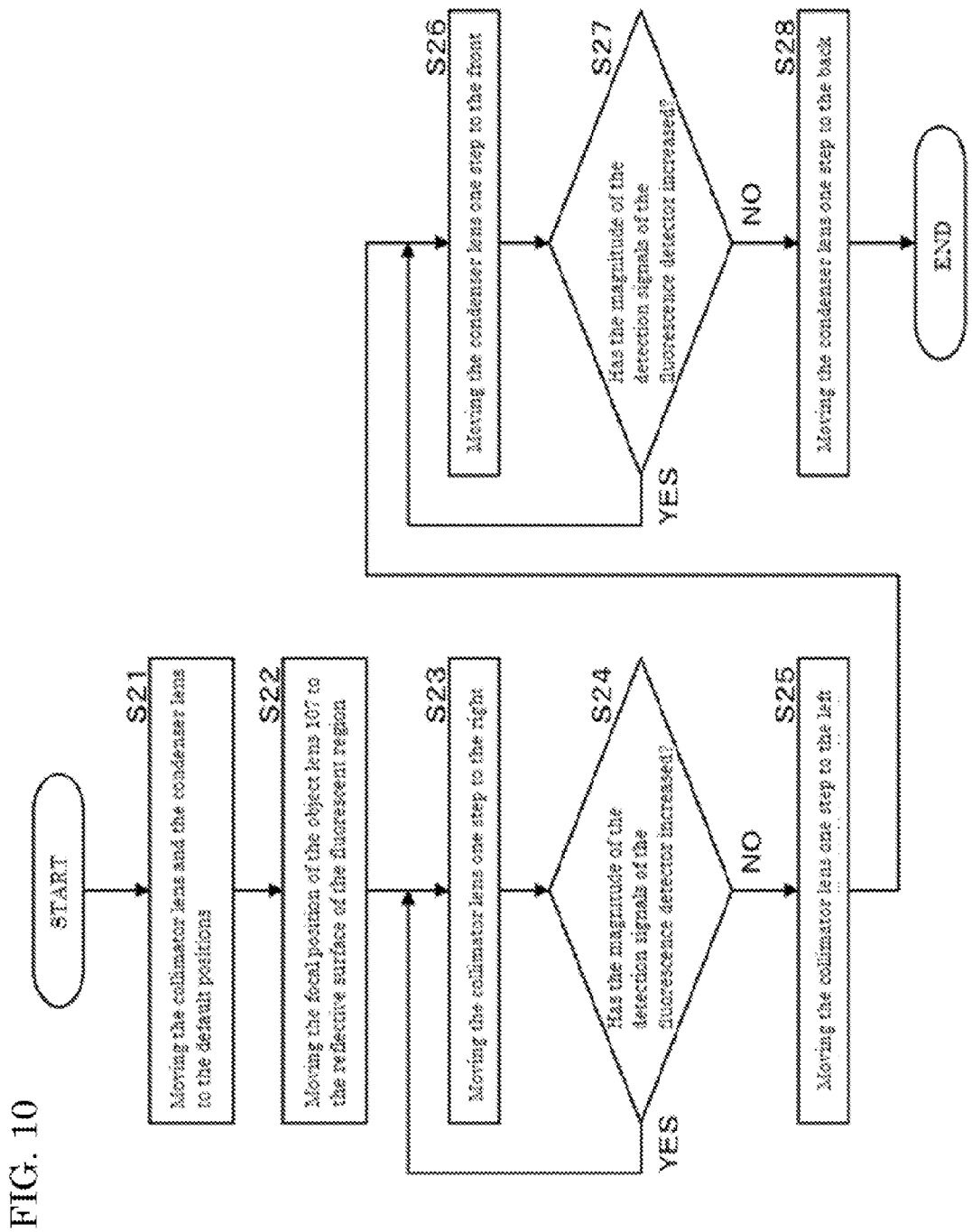
FIG. 10 is a flowchart showing how the controller drives lens actuators in the second embodiment.

FIG. 10 is a flowchart showing how controller 205 drives lens actuators 124 and 125. The driving is performed prior to the process of setting the fluorescent signal gain factor G and the threshold Vsh shown in FIG. 8A.

First, controller 205 moves collimator lens 104 and condenser lens 110 to the default positions via lens driving circuit 206 (S21). The default position of collimator lens 104 is the leftmost (close to quarter wavelength plate 105) in the travel range of collimator lens 104. The default position of condenser lens 110 is the rearmost (close to dichroic prism 106) in the travel range of condenser lens 110. When collimator lens 104 is in the default position, the excitation light incident from PBS 103 is converted into parallel light by collimator lens 104.

Next, controller 205 moves the focal position of object lens 107 to fluorescent region A1 and drives object lens actuator 122 so as to focus the excitation light on reflective surface 11a of fluorescent region A1 (S22).

Next, controller 205 moves collimator lens 104 one step to the right (toward PBS 103) (S23), and determines whether the magnitude of the detection signals of fluorescence detector 111 has increased or not (S24). If the magnitude of the detection signals of fluorescence detector 111 has increased (S24: YES), the process returns to S23. If the magnitude of the detection signals of fluorescence detector 111 has not increased (S24: NO), controller 205 moves collimator lens 104 one step to the left (toward quarter wavelength plate 105) (S25). As a result, collimator lens 104 is in the position where the fluorescence is detected most strongly. In other words, the focal position of the excitation light can be located on fluorescent bottom surface portion 15a.

In the case that in biosensor substrate 10, the width d3 shown in FIG. 7A or 7B is uneven, bottom surface portions 13a of wells 13 may not be included in the range of the focal depth when the excitation light is focused on reflective surface 11a as in the first embodiment. Even in such a case, collimator lens 104 is moved as described above, so that the focal position of the excitation light can be located on bottom surface portion 13a. This enables fluorescence detection device 2 to detect malaria parasites with higher accuracy.

Next, controller 205 moves condenser lens 110 one step to the front (toward fluorescence detector 111) (S26), and determines whether the magnitude of the detection signals of fluorescence detector 111 has increased or not (S27). If the magnitude of the detection signals of fluorescence detector 111 has increased (S27: YES), the process returns to S26. If the magnitude of the detection signals of fluorescence detector 111 has not increased (S27: NO), controller 205 moves condenser lens 110 one step to the back (toward dichroic prism 106) (S28). As a result, condenser lens 110 is in the position where the fluorescence is detected most strongly. In other words, the position of the fluorescence collected to fluorescence detector 111 can be set on fluorescent bottom surface portion 15a on biosensor substrate 10.

Adjusting the position of condenser lens 110 in this manner results in an increase in the magnitude of the detection signals from fluorescence detector 111 corresponding to the fluorescence generated in the erythrocytes infected with malaria parasites. This enables fluorescence detection device 2 to detect the malaria parasites with higher accuracy.

After collimator lens 104 and condenser lens 110 are thus positioned, the process shown in FIG. 8A for setting the fluorescent signal gain factor G and the threshold Vsh is performed, and then well region A3 is detected for fluorescence. The setting process shown in FIG. 10 is performed for fluorescent bottom surface portion 15a coated with the fluorescent material. The depth position of fluorescent bottom surface portion 15a is substantially equal to that of bottom surface portions 13a of wells 13. Therefore, the positions of collimator lens 104 and condenser lens 110, which are set in the process shown in FIG. 10, are also applicable to the depth position of bottom surface portions 13a of wells 13.

Thus, even if the distance between reflective surface 11a and bottom surface portions 13a of wells 13 differs in each produced biosensor substrate 10, the excitation light can be properly applied to the samples by arbitrarily changing the focal position of the excitation light (S23-S25). This increases the magnitude of the signals that fluorescence detector 111 outputs. In addition, even if the distance between reflective surface 11a and bottom surface portions 13a of wells 13 differs in each produced biosensor substrate 10, the fluorescence from an appropriate depth can be collected to fluorescence detector 111 by arbitrarily changing the position of condenser lens 110 (S26-S28). This increases the magnitude of the signals that fluorescence detector 111 outputs. Thus, collimator lens 104 and condenser lens 110 are positioned as set in the process of FIG. 10, and well region A3 is detected for fluorescence, so that the fluorescence generated in the erythrocytes infected with malaria parasites can be detected with higher accuracy than in the first embodiment.

It is alternatively possible to manage the conditions of the biosensor substrate by the magnitude of the fluorescent signal gain G, after collimator lens 104 and condenser lens 110 are positioned and well region A3 is detected for fluorescence. In the case that the signal strength decreases by the degradation of the fluorescent indicator previously coated on the biosensor substrate, the signal strength detected in fluorescent bottom surface portion 15a decreases with the degradation. As the signal strength decreases, the fluorescent signal gain G increases with the degradation.

Therefore, the device may be preset to determine the upper limit of the magnitude of the fluorescent signal gain G and to limit the use of the biosensor substrate when the upper limit is exceeded. When the fluorescent signal gain G exceeds the set value, or when the signal strength of the previously coated fluorescent indicator decreases to a predetermined level, the device may indicate abnormality of the biosensor substrate to the user and remove the substrate from the device.

<Modified Example>

Figure 11A:
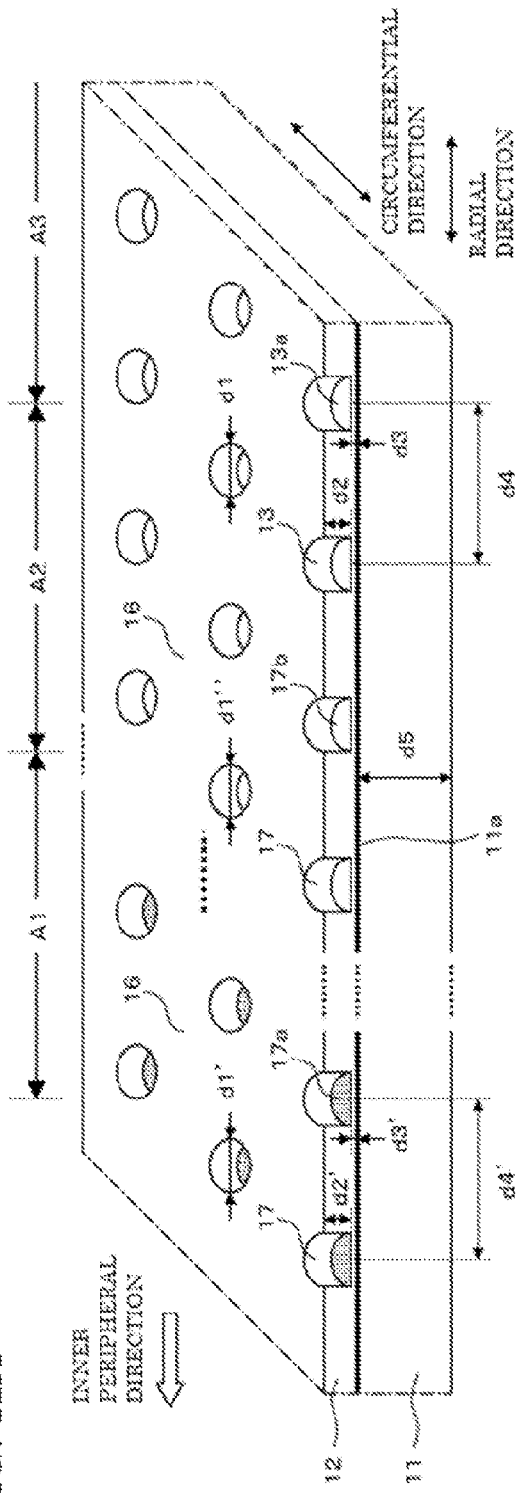
FIG. 11A is a configuration of a biosensor substrate.

Fluorescent bottom surface portion 15a and non-fluorescent bottom surface portion 15b are formed on the bottom surface of grooves 15 in the first and second embodiments, but may alternatively be formed on the bottom surface of wells 17 as shown in FIG. 11A. Wells 17 are columnar just like wells 13. In this case, too, the bottom surface of wells 17 in fluorescent region A1 is referred to as fluorescent bottom surface portion 17a just like fluorescent bottom surface portion 15a, and the bottom surface of wells 17 in non-fluorescent region A2 is referred to as non-fluorescent bottom surface portion 17b just like non-fluorescent bottom surface portion 15b. Wells 17 in non-fluorescent region A2 have a diameter d". Note that the dimensions d1 to d5 and d1' to d4' shown in FIG. 11A are identical to those in the first embodiment, and that the following relation is satisfied: d1=d1'=d".

Figure 11B:
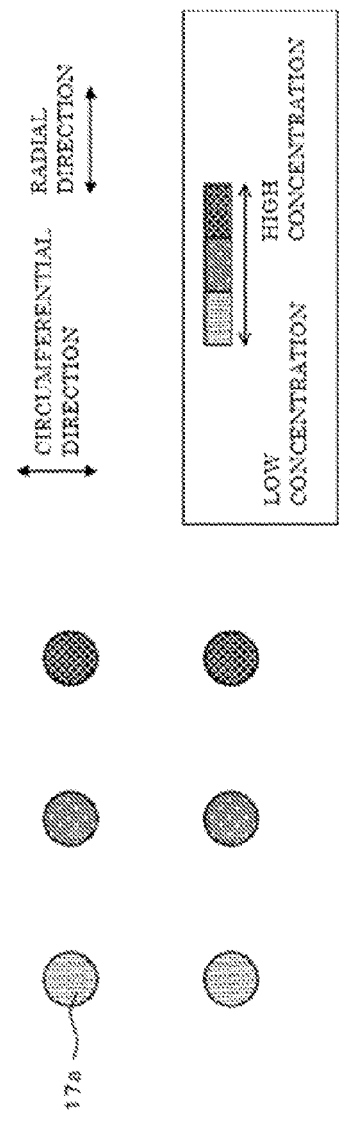
FIG. 11B is a schematic configuration of the concentrations of fluorescent materials coated on a fluorescent bottom surface portion in a modified example of the second embodiment.

In the case that wells 17 are formed in fluorescent region A1 and non-fluorescent region A2 as shown in FIG. 11A, the concentration of the fluorescent material coated on fluorescent bottom surface portion 17a of wells 17 may be gradually changed depending on the stage of infection with malaria parasites as shown in FIG. 11B. In the erythrocytes infected with malaria parasites, as the infection make progress, the amount of parasites increases and the magnitude of the fluorescence generated from the erythrocytes increases. Therefore, as shown in FIG. 11B, the concentration of the fluorescent material coated on fluorescent bottom surface portion 17a is divided into, for example, three stages. In this case, the lowest concentration is made equal to the concentration of fluorescent bottom surface portion 15a shown in the above-described embodiment.

For example, three concentric regions each having a plurality of wells 17 are formed in the radial direction in fluorescent region A1 of biosensor substrate 10. Fluorescent materials different in concentration are applied to the respective concentric regions. Consequently, wells 17 in the same concentric region are coated with a fluorescent material having the same concentration. In other words, wells 17 in adjacent concentric regions are coated with fluorescent materials different in concentration.

In this case, controller 205 scans wells 17 held in the region having the lowest concentration of the three concentric regions, and executes the process shown in FIG. 8A so as to set the fluorescent signal gain factor G and the threshold Vsh. Next, controller 205 sequentially scans wells 17 held in the concentric region coated with the fluorescent material having the highest concentration, and the wells 17 held in the concentric region coated with the fluorescent material having the medium concentration. Controller 205 then acquires maximum values V1a and V1b of the detection signals of the fluorescence in these regions, and further acquires values V1a' and V1b', which are the product of the fluorescent signal gain factor G and the maximum values V1a and V1b, respectively. Then, controller 205 sets a threshold Vshb between the target value Vt and the value V1b', and also sets a threshold Vsha between the value V1b' and the value V1a'. If the product of the fluorescent signal gain factor G and the detection signals of the fluorescence obtained when well region A3 is scanned with the excitation light exceeds the threshold Vsh, controller 205 determines that the fluorescence has been generated from the malaria parasites. Furthermore, controller 205 determines the infection with malaria parasites to be in the early stage when the product is between the thresholds Vsh and Vshb; to be in the intermediate stage when the product is between the thresholds Vshb and Vsha; and to be in the final stage when the product is greater than the threshold Vsha.

Thus, in this modified example, the stage of infection with malaria parasites can be figured out from the magnitude of the fluorescence generated in the samples. In addition, the conditions of detection targets other than malaria parasites can be figured out from the difference in detection intensity.

Figure 12A:
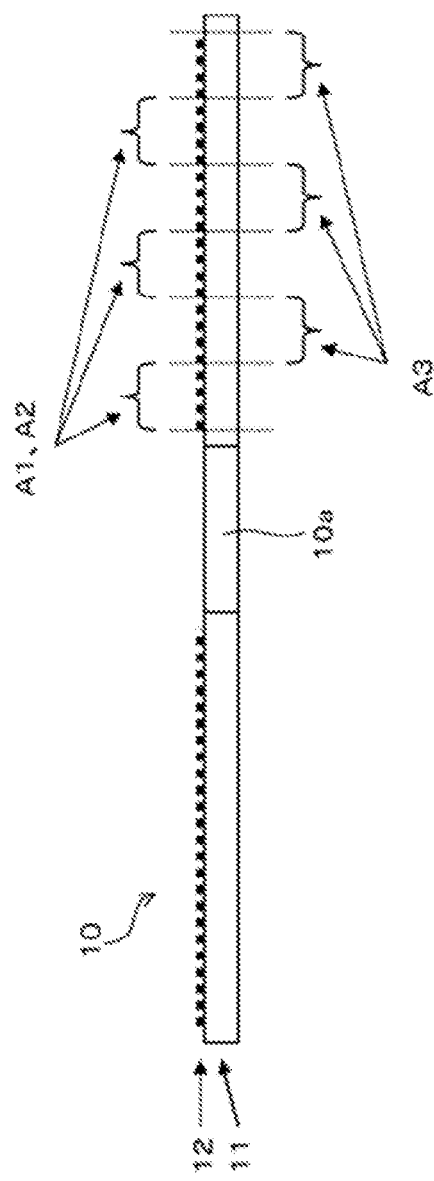
FIGS. 12A and 12B are configurations of the biosensor substrate of the modified example.
Figure 12B:
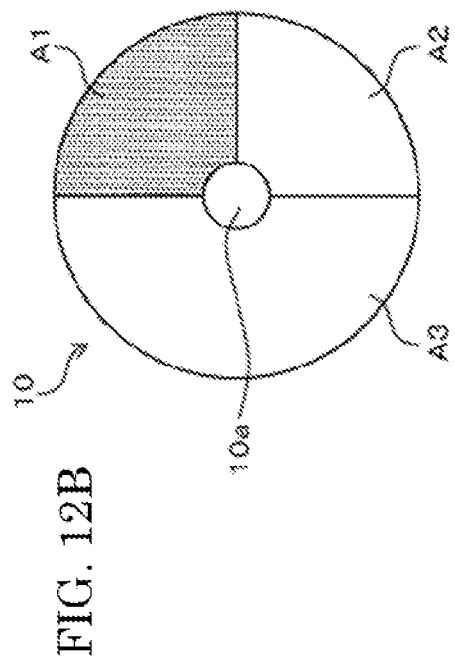

In the first and second embodiments, fluorescent region A1 and non-fluorescent region A2 are formed near the inner periphery of biosensor substrate 10 as shown in FIG. 1. Alternatively, they may be formed near the outer periphery or between the inner and outer peripheries of biosensor substrate 10. Alternatively, a region including fluorescent region A1 and non-fluorescent region A2 may be regularly alternated with well region A3 in the radial direction as shown in FIG. 12A. Alternatively, fluorescent region A1, non-fluorescent region A2, and well region A3 may be formed at respectively predetermined angles with respect to the center of biosensor substrate 10 as shown in FIG. 12B. In this case, fluorescent region A1 may be used as a specific region of the wells.

The fluorescence detection device may be configured to read system information and other information to identify the position of fluorescent region A1 and hence to identify a well away from fluorescent region A1 by a predetermined distance. Fluorescent region A1 in which the fluorescent material is buried and the well bottom surface are nearly equidistant from the reflective surface, so that the focal position of the excitation light can be located on bottom surface portion 13a. As a result, well positions can be identified more securely. It is also possible to place a single well in fluorescent region A1. In this case, fluorescent region A1 and the well correspond one-to-one with each other, making it easier to detect the position of the well.

In the case that biosensor substrate 10 is warped, the magnitude of the fluorescence generated in the samples differs depending on the position in the radial direction. When, however, biosensor substrate 10 is configured as shown in FIG. 12A, the magnitude of the fluorescence generated in the samples can be amplified to the same level as the fluorescence generated in a nearby fluorescent region A1. This standardizes the magnitude of the fluorescence generated in the samples in different positions in the radial direction.

On the other hand, when biosensor substrate 10 is configured as shown in FIG. 12A, it is possible to detect the warpage of biosensor substrate 10 from the inner to the outer periphery. This allows optical corrections such as tilting object lens 107 or the optical system including object lens 107. For example, when the fluorescence generated in the three fluorescent regions A1 shown in FIG. 12A decreases from the inner to the outer periphery, object lens 107 is tilted to increase the magnitude of the fluorescence generated in fluorescent regions A1 in the middle and outer peripheries. In this case, the tilt angle of object lens 107 in each position on biosensor substrate 10 is acquired on the basis of the tilt angle of object lens 107 with respect to fluorescent regions A1 in the middle and outer peripheries. Then, the tilt angle of object lens 107 with respect to well regions A3 is set on the basis of the acquired tilt angle. As a result, the fluorescence generated in well regions A3 can be detected with high accuracy even if biosensor substrate 10 is warped.

<Third Embodiment>

Figure 13:
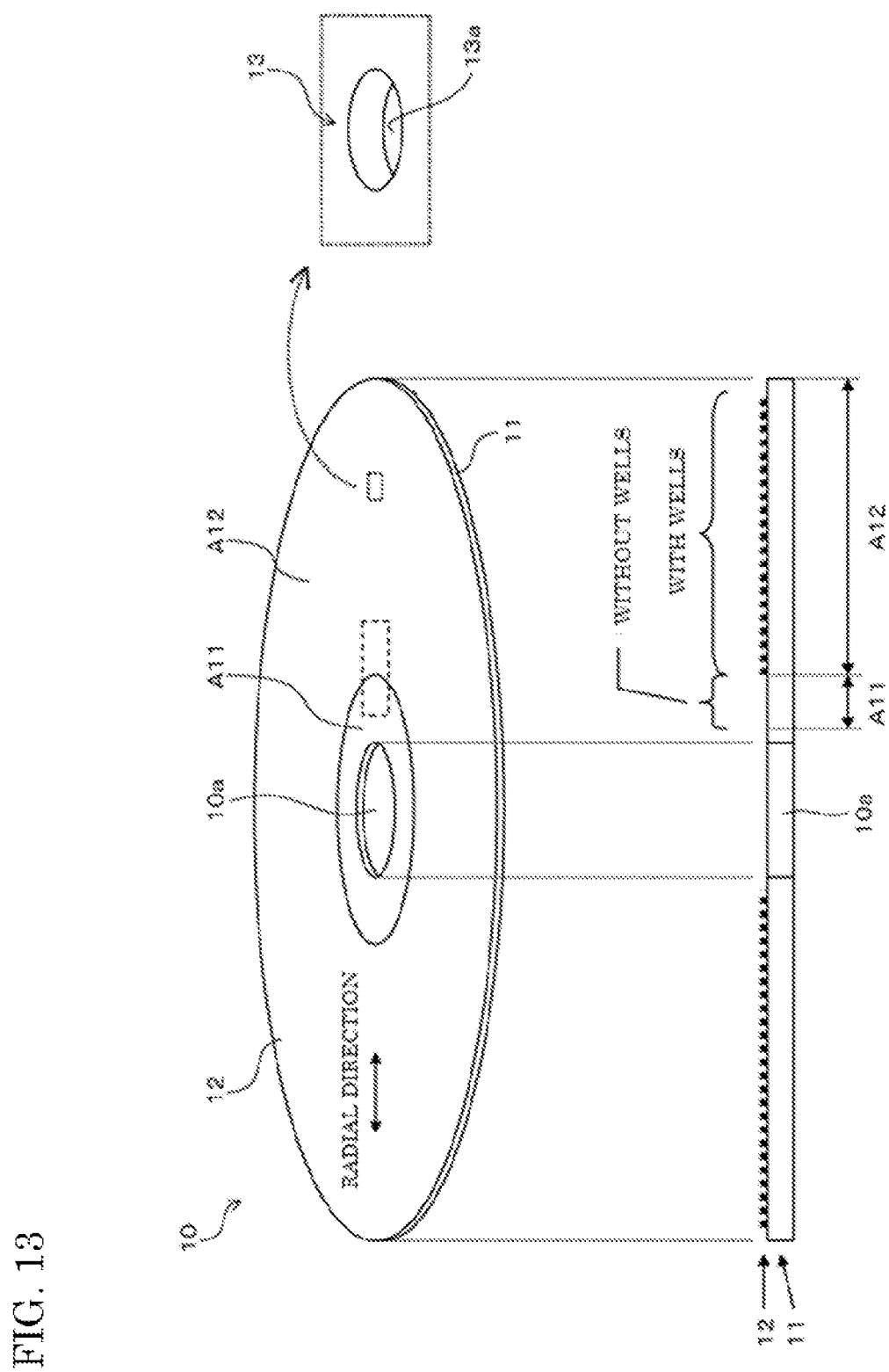
FIG. 13 is a schematic configuration of a biosensor substrate of a third embodiment.

FIG. 13 is a schematic configuration of biosensor substrate 10 of the present embodiment. Biosensor substrate 10 is used, for example, to detect erythrocytes infected with malaria parasites in human blood.

As shown in the perspective view of the upper part of FIG. 13, biosensor substrate 10 is disc-shaped like an optical disc (such as a CD or DVD), and has circular hole 10a at its center. Biosensor substrate 10 includes base substrate 11 and well layer 12 formed on the upper surface of base substrate 11.

As shown in the perspective view of the upper part and the sectional view of the lower part of FIG. 13, well layer 12 is divided into two regions: system calibration region A11 and well region A12 in this order from the center to the periphery. Each region is set before use. When biosensor substrate 10 is in use, samples are dropped in well region A12, but not in system calibration region A11. Thus, when biosensor substrate 10 is in use, the samples are held in wells 13, and the fluorescence generated from the samples is detected.

Well region A12 contains a plurality of minuscule wells 13 each having a columnar hollow. Such well 13 is shown in the enlarged view on the extreme right of FIG. 13. Wells 13 are substantially concentrically arranged from the center of biosensor substrate 10 outward. Each well 13 has bottom surface portion 13a sunken below the top surface of well layer 12. Bottom surface portion 13a has a diameter and a height to hold a drop of each sample. System calibration region A11 does not have wells 13, and has a ring-shaped recess portion 15, which will be described later with reference to FIG. 14A.

FIG. 14A is an enlarged view of the dotted-line rectangle shown in the perspective view of FIG. 13, and FIG. 14B is an enlarged view of the dotted-line rectangle shown in FIG. 14A.

As shown in FIG. 14B, the upper surface of base substrate 11 (the surface on the well layer 12 side) is provided with a spiral track as in an optical disc. The track is formed of meandering (wobbled) grooves, which store address information for locating positions on the surface of biosensor substrate 10. The track portions corresponding to system calibration region A11 store not only the address information but also peculiar information held in the meandering-shaped grooves. This peculiar information is unique to biosensor substrate 10 and is arbitrarily used to detect the fluorescence generated from cells as test objects (hereinafter, referred to as the system information).

FIG. 14C shows the data format of the information stored in the track portions corresponding to system calibration region A11. In FIG. 14C, one frame contains a synchronous signal, address information, system information, and error correction code (ECC). The frame shown in FIG. 14C is stored repeatedly and continuously in the entire track portions corresponding to system calibration region A11. The synchronous signal is composed of, for example, a continuation of a 4T signal in order to identify the beginning of the address.

The system information contains, for example, the information about the area on which the fluorescent material is previously coated; the information about the position under which the track first enters wells 13 and the position from which the track finally leaves wells 13 on biosensor substrate 10; the information to identify the number of wells 13 held on biosensor substrate 10; the manufacturing date, the expiry date, and the manufacturer of biosensor substrate 10; and the information to show the object to be tested on biosensor substrate 10. The information about the area to which the fluorescent material is previously applied is identified by the address information.

It is possible to access the area on which the fluorescent material is coated and to set a reproduction signal level or to detect the condition of the biosensor substrate. The start and end positions of wells 13 are identified by the address information corresponding to these positions. The start position of wells 13 is used, for example, to make the scanning position of the excitation light coincide with the start position when wells 13 are scanned, or to identify the region including system calibration region A11 and unused region A13. The end position of wells 13 is used, for example, to determine whether all wells 13 have been scanned or not. The information about the number of wells 13 is used, for example, to acquire the number of wells 13 remaining to be scanned. The start and end positions of the address can be used to calculate the time required for detection so as to inform the user of the progress of the calculation. The manufacturing date and the expiry date of biosensor substrate 10 are used to determine whether biosensor substrate 10 is to be the target of fluorescence detection or not. This is because in the case that bottom surface portions 13a of wells 13 is previously coated with a fluorescence material for fluorescently-labeled the test object, when the expiry date has passed, the fluorescence material may not be sensitive enough for proper detection. The information to identify the manufacturer is used, for example, to confirm the reliability of biosensor substrate 10 or to set a parameter for each manufacturer. The information to indicate the test object is used in the following situations by the device. It is determined whether fluorescence detection on biosensor substrate 10 is possible or not. When the fluorescence detection is impossible, it is determined whether biosensor substrate 10 is removed or a warning is issued to the user, or a detecting means is switched depending on the test object, such as changing the wavelength of the excitation light, which will be described later. Such system information is collectively stored in the system information area in a frame.

Similar to a CD or DVD, the address information and the system information are reproduced by scanning the track at constant linear velocity with excitation light (described later). The track is extended spirally from the innermost periphery to the outermost periphery of biosensor substrate 10. The track continuously stores the address information for identifying positions. As shown in FIG. 14A, between base substrate 11 and well layer 12, there is provided reflective film 14. The formation of reflective film 14 on the track portions on the upper surface of base substrate 1 results in the formation of reflective surface 11a on the upper surface of base substrate 11. Reflective surface 11a is the interface between reflective film 14 and base substrate 11.

Wells 13 are arranged at predetermined intervals on the upper surface of well region A12. Bottom surface portion 13a of each well 13 is slightly higher than reflective film 14 so as to be away from the upper surface of reflective film 14. Recess portion 15 with a predetermined width is formed on the upper surface of system calibration region A11 in the radial direction. Similar to bottom surface portions 13a of wells 13, bottom surface portion 15a of recess portion 15 is slightly higher than reflective film 14 so as to be away from the upper surface of reflective film 14.

Unused region A13 is formed between system calibration region A11 and well region A12 (outside recess portion 15). The track portions corresponding to unused region A13 store not only the address information but also dummy information in the meandering-shaped grooves. FIG. 14D shows the data format of the track portions corresponding to unused region A13. In the data format of unused region A13, the dummy information portion is provided instead of the system information portion provided in the data format of system calibration region A11 shown in FIG. 14C. The dummy information portion stores predetermined dummy information. More specifically, "0" is used as the dummy information.

Unused region A13 is set so that its system information is not overlapped with that of well region A12 in consideration of the production tolerance or eccentricity of biosensor substrate 10. Thus, unused region A13 is not a region to be accessed in order to acquire information. The edge of well region A12 has a poor shape accuracy of the substrate, and hence, is likely to cause noise. Therefore, unused region A13 functions as a buffer region. More specifically, unused region A13 has a width of 50 µm to 500 µm in the radial direction in consideration of the production tolerance and eccentricity.

In FIG. 14A, each well 13 has a diameter d1, and a height d2. Bottom surface portion 13a and reflective surface 11a have a distance d3 between them. Wells 13 have a distance d4 between each other. Similarly, recess portion 15 have a height d2'. Bottom surface portion 15a and reflective surface 11a have a distance d3' between them. Base substrate 11 has a thickness d5, and reflective surface 11a has a track pitch d6. Unused region A13 has a width d7 in the radial direction. In the present embodiment, the dimensions d1 to d7 are set to 100 µm, 50 µm, 2 µm, 300 µm, 0.6 mm, 1 µm, and 100 µm, respectively. Furthermore, the dimensions d2' and d3' are set to 50 µm and 2 µm, respectively, which are identical to the dimensions d2 and d3. The reflectance of excitation light (described later) for reflective film 14 is set to 3 to 4%.

In the present embodiment, base substrate 11 is made of polycarbonate. Well layer 12 is made of ultraviolet curable resin. Reflective film 14 is made of metal such as aluminum or a silver alloy; a dielectric such as niobium oxide; or a wavelength selection film. Base substrate 11 may alternatively be made, for example, of polymethyl methacrylate, amorphous polyolefin, or a transparent material such as a biodegradable material besides polycarbonate. Well layer 12 may alternatively be made, for example, of silicone, polycarbonate, polymethyl methacrylate, or amorphous polyolefin. Reflective film 14 is set to have a thickness of, for example, 5 nm to 20 nm so as to have a desired reflectance for the wavelength of the excitation light. It is also preferable that the material and thickness of reflective film 14 be set to have a reflectance for the wavelength of the excitation light and a low reflectance for the wavelength of the fluorescence.

FIGS. 15A-15D show how to form biosensor substrate 10.

First, as shown in FIG. 15A, base substrate 11 is formed by injection molding. Base substrate 11 has a thickness d5, and is provided with a series of track portions on its upper surface. Next, as shown in FIG. 15B, reflective film 14 is formed on the upper surface of base substrate 11, so that reflective surface 11a is formed on the track portions on the upper surface of base substrate 11. Then, as shown in FIG. 15C, bottom surface layer 12a is spin-coated on the upper surface of reflective film 14. Next, as shown in FIG. 15D, top surface layer 12b having a thickness d2 is formed by 2P molding on the upper surface of bottom surface layer 12a. Consequently, a plurality of wells 13 and recess portion 15 are formed, and well layer 12 is formed by a combination of bottom surface layer 12a and top surface layer 12b.

When top surface layer 12b is formed as shown in FIG. 15D, if top surface layer 12b is displaced in the radial direction due to the error in 2P molding, the track portions corresponding to system calibration region A11 might overlap wells 13 in well region A12. In the present embodiment, however, system calibration region A11 and well region A12 are separated by unused region A13 provided therebetween. Therefore, even if top surface layer 12b is displaced in the radial direction, the track portions corresponding to system calibration region A11 are prevented from overlapping wells 13.

Figure 16:
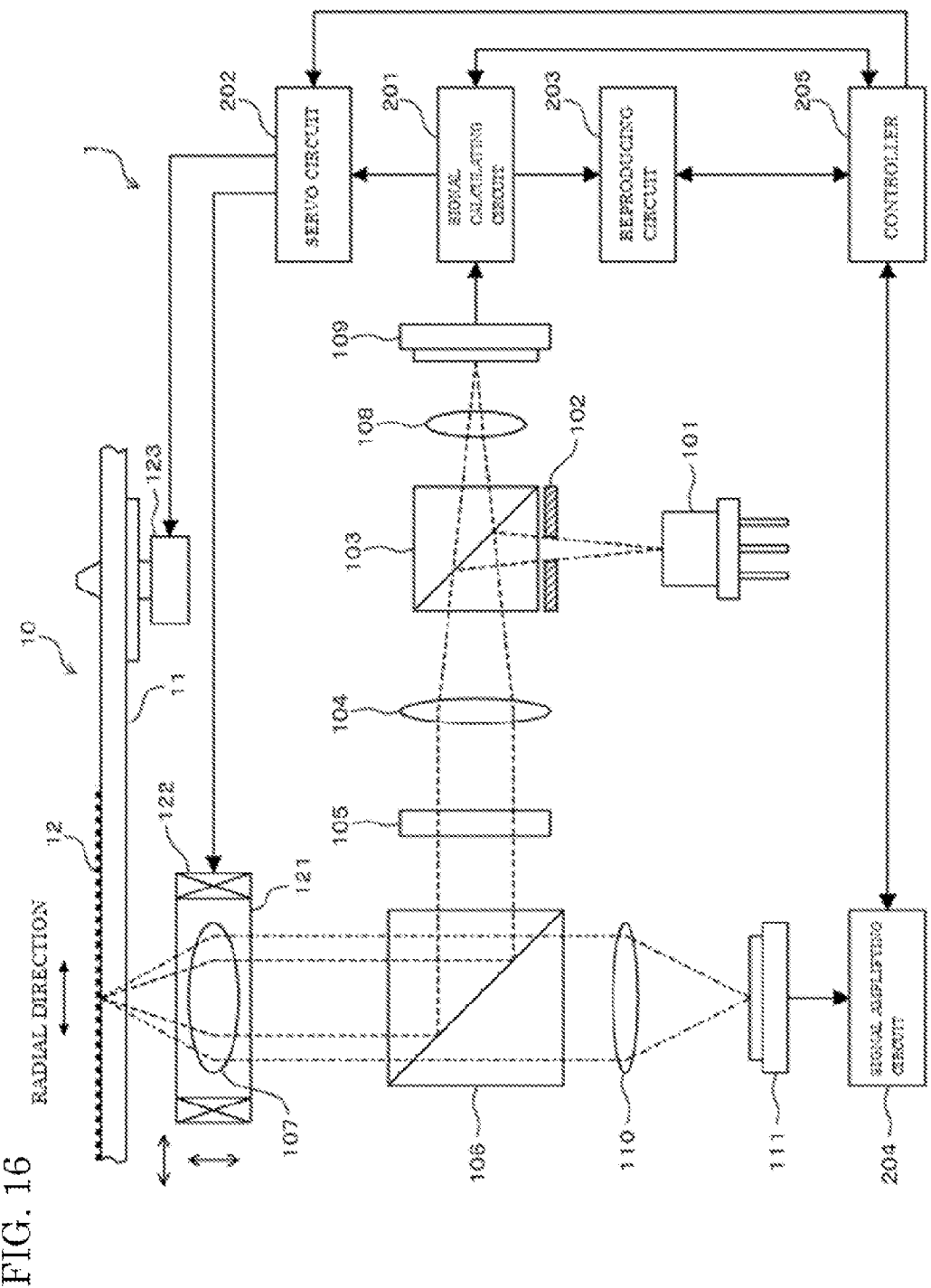
FIG. 16 is a configuration of a fluorescence detection device of the third embodiment.

FIG. 16 is a configuration of fluorescence detection device 1 of the present embodiment. Fluorescence detection device 1 is used, for example, to determine whether the erythrocytes held in wells 13 of biosensor substrate 10 are infected with malaria parasites or not.

Samples are prepared by fluorescently-labeled test objects prior to the use of fluorescence detection device 1 and are placed into wells 13 of biosensor substrate 10. The test objects used in the present embodiment are erythrocytes approximately 10 µm in diameter and approximately 2 µm in thickness. The erythrocytes, which may or may not be infected with malaria parasites are parallel-arranged on bottom surface portion 13a of each well 13, which is 100 µm in diameter. The nuclei of infected erythrocytes will be fluorescently-labeled. Biosensor substrate 10 with the samples held thereon is set on rotation device 123 (turntable) of fluorescence detection device 1 by aligning hole 10a (see FIG. 13) with the center of rotation device 123. Then, the measurement is started.

The optical system of fluorescence detection device 1 includes semiconductor laser 101, aperture 102, polarizing beam splitter (PBS) 103, collimator lens 104, quarter wavelength plate 105, dichroic prism 106, object lens 107, anamorphic lens 108, light detector 109, condenser lens 110, and fluorescence detector 111. Besides the optical system, fluorescence detection device 1 further includes holder 121, object lens actuator 122, rotation device 123, signal calculating circuit 201, servo circuit 202, reproducing circuit 203, signal amplifying circuit 204, and controller 205.

The optical system, holder 121, and object lens actuator 122 of fluorescence detection device 1 are accommodated in a housing like an existing optical pickup device used for recording and reproduction in a CD or DVD. The housing can be moved in the radial direction of biosensor substrate 10 by a predetermined guide mechanism. Servo circuit 202 also controls the movement of this housing.

Semiconductor laser 101 emits laser light (hereinafter, the excitation light) with a wavelength of approximately 405 nm. The excitation light referred to in the present embodiment is one example of the irradiation light described in the claims. In FIG. 16, a part of the excitation light emitted by semiconductor laser 101 passes through aperture 102 and is guided to biosensor substrate 10, the excitation light is shown by dotted lines. Aperture 102 has a circular opening with a predetermined diameter so as to limit the diameter of the excitation light. Semiconductor laser 101 is positioned so that the excitation light emitted from semiconductor laser 101 can be s-polarized with respect to PBS 103. As a result, the excitation light emitted from semiconductor laser 101 is reduced in diameter by aperture 102, then is reflected by PBS 103, and is incident on collimator lens 104.

Collimator lens 104 converts the excitation light incident from PBS 103 into parallel light having a predetermined diameter. Quarter wavelength plate 105 converts the excitation light incident from collimator lens 104 into circularly polarized light. Quarter wavelength plate 105 also converts the excitation light incident from dichroic prism 106 into linearly polarized light, which is at right angles to the direction in which the excitation light incident from collimator lens 104 is polarized. As a result, the excitation light incident on PBS 103 from collimator lens 104 passes through PBS 103.

Dichroic prism 106 is configured to reflect laser light with a wavelength of approximately 405 nm and to transmit laser light with a wavelength of approximately 450 to 540 nm. Therefore, the excitation light incident from quarter wavelength plate 105 is reflected by dichroic prism 106 and then is incident on object lens 107.

Object lens 107 is configured to converge excitation light on biosensor substrate 10 properly. More specifically, object lens 107 is configured to converge the excitation light incident from dichroic prism 106 with a predetermined numerical aperture (NA), which is 0.34 in this case. The diameter of the excitation light incident on object lens 107 is determined by the diameter of aperture 102. The focal depth of the excitation light converged by object lens 107 is determined by the NA of the excitation light. The focal depth of the excitation light will be described later with reference to FIGS. 18A and 18B.

Object lens 107, which is held in holder 121, is driven by object lens actuator 122 in the focusing direction (the direction perpendicular to biosensor substrate 10) and the tracking direction (the radial direction of biosensor substrate 10). In short, object lens 107 is driven to follow the track formed of the grooves while the excitation light is focused on reflective surface 11a of biosensor substrate 10. Some of the excitation light focused on reflective surface 11a is reflected by reflective surface 11a, but the most of it passes through reflective surface 11a.

When the excitation light converged by object lens 107 scans the positions corresponding to well region A12, the excitation light that has passed through reflective surface 11a is applied to the portion of well layer 12 corresponding to well region A12. As shown in FIG. 14A, the portion of well layer 12 corresponding to well region A12 includes a region having wells 13 and a region not having wells 13. Since biosensor substrate 10 is rotated in the circumferential direction, the excitation light applied to wells 13 in well layer 12 is reflected by bottom surface portions 13a of wells 13 and the upper surface of well layer 12 not having wells 13. Furthermore, the excitation light may be scattered or reflected in different directions when scanning the stepped portion at the boundary between bottom surface portion 13a and the upper surface of well layer 12.

On the other hand, when the excitation light converged by object lens 107 scans the positions corresponding to system calibration region A11, the excitation light that has passed through the reflective surface 11a is applied to the portion of well layer 12 corresponding to system calibration region A11. Recess portion 15 is alone formed in the portion of well layer 12 corresponding to system calibration region A11 as shown in FIG. 14A. In this case, regardless of the position to which the excitation light is applied, the excitation light reflected by well layer 12 has a substantially uniform intensity. Furthermore, recess portion 15, which do not include stepped portions in the scanning direction of the excitation light, prevent the excitation light from being scattered or reflected in different directions, and allow it to be reflected in an optically stable manner.

The excitation light reflected by reflective surface 11a and the excitation light reflect by well layer 12 (hereinafter, collectively referred to as the "reflected excitation light") is reflected by dichroic prism 106, convert into linearly polarized light by quarter wavelength plate 105, and made into convergent light by collimator lens 104. The reflected excitation light incident on PBS 103 from collimator lens 104 passes through PBS 103 as described above.

Anamorphic lens 108 introduces astigmatism to the reflected excitation light which is incident from PBS 103. The reflected excitation light that has passed through anamorphic lens 108 is incident on light detector 109. Light detector 109 includes a four-quandrant sensor for receiving the reflected excitation light on its light-receiving surfaces. The detection signals of light detector 109 are entered to signal calculating circuit 201.

On the other hand, when the excitation light converged by object lens 107 scans the positions corresponding to wells 13, a part of the excitation light applied to biosensor substrate 10 has passed through reflective surface 11a and reaches bottom surface portions 13a of wells 13. When the excitation light is applied to the erythrocytes fluorescently-labeled and parallel-arranged on bottom surface portion 13a, the erythrocytes infected with malaria parasites fluoresce. This fluorescence shown by chain lines in FIG. 16 has a larger numerical aperture (NA) than the excitation light. Therefore, between object lens 107 and dichroic prism 106, the fluorescent light has a larger beam diameter than the excitation light. The NA of the fluorescent light is, for example, 0.65. Furthermore, the fluorescence has a wavelength of 450 to 540 nm in the present embodiment, which is different from that of the excitation light. In contrast, fluorescence is not generated in the erythrocytes uninfected with malaria parasites because they are not fluorescently-labeled. Thus, erythrocytes infected with malaria parasites and those uninfected can be distinguished.

The fluorescence incident on dichroic prism 106 from object lens 107 passes through dichroic prism 106. The fluorescence incident from dichroic prism 106 is collected to condenser lens 110, which leads the fluorescence to fluorescence detector 111. Fluorescence detector 111 includes a sensor for receiving fluorescence on its light-receiving surfaces. The detection signals of fluorescence detector 111 are entered to signal amplifying circuit 204.

Signal calculating circuit 201 generates a focus error signal FE and a tracking error signal TE (both described later) from the detection signals of light detector 109. Signal calculating circuit 201 also generates wobble signals corresponding to the meandering shape of the track from the detection signals of light detector 109. Servo circuit 202 controls the driving of object lens actuator 122 using the focus error signal FE and the tracking error signal TE sent from signal calculating circuit 201. Servo circuit 202 also controls rotation device 123 using the wobble signals sent from signal calculating circuit 201 so that biosensor substrate 10 can be rotated at constant linear velocity. Reproducing circuit 203 demodulates the wobble signals sent from signal calculating circuit 201, and generates reproduction data. Signal amplifying circuit 204 amplifies the detection signals of fluorescence detector 111.

Controller 205 controls signal calculating circuit 201, servo circuit 202, reproducing circuit 203, and other units of fluorescence detection device 1. Controller 205 detects the fluorescence generated in well region A12 on the basis of the output signal of signal amplifying circuit 204. Controller 205 then determines the positions where fluorescence is generated, on the basis of the detected fluorescence and the reproduction data (address information) of the track sent from reproducing circuit 203. Controller 205 also stores, in its internal memory, the address information corresponding to the positions in well region A12 where the fluorescence is generated. Furthermore, controller 205 acquires the reproduction data (system information) from reproducing circuit 203 and holds it in the internal memory.

FIG. 17A is a schematic diagram of a circuit that generates the focus error signal FE and the tracking error signal TE. This circuit is contained in signal calculating circuit 201.

Light detector 109 includes a four-quandrant sensor for receiving the reflected excitation light on its light-receiving surfaces as described above. The four-quandrant sensor is configured to output detection signals S1-S4 on the basis of the beam spot of the reflected excitation light received on the upper left-, upper right-, lower right-, and lower left-hand light-receiving surfaces, respectively. In FIG. 17A, the horizontal direction of the light-receiving surfaces of light detector 109 corresponds to the radial direction of the disc. The focus error signal FE and the tracking error signal TE are generated by the astigmatism method and the one-beam push-pull method, which are used in existing optical disc devices.

Signal calculating circuit 201 includes adders 301-304, and subtractors 305 and 306. Adder 301 outputs the sum of detection signals S1 and S3 to subtractor 305. Adder 302 outputs the sum of detection signals S2 and S4 to subtractor 305. Adder 303 outputs the sum of detection signals S1 and S4 to subtractor 306. Adder 304 outputs the sum of detection signals S2 and S3 to subtractor 306.

Subtractor 305 subtracts the output signals of adders 301 and 302, and outputs the focus error signal FE. Subtractor 306 subtracts the output signals of adders 303 and 304, and outputs the tracking error signal TE. Thus, the focus error signal FE and the tracking error signal TE are calculated by the following Formulas (1) and (2), respectively.

$$FE=(S1+S3)-(S2+S4) \quad (1)$$

$$TE=(S1+S4)-(S2+S3) \quad (2)$$

When the focal position of object lens 107 is located on reflective surface 11a, the beam spot on the four-quandrant sensor of light detector 109 becomes a circle of least confusion, and the focus error signal FE in Formula (1) has a value of 0. When the focal position of object lens 107 is just above the track portions of reflective surface 11a, the beam spot on the four-quandrant sensor of light detector 109 falls equally between the two left-hand sensors and the two right-hand sensors, and the tracking error signal TE in Formula (2) has a value of 0.

The focus error signal FE and the tracking error signal TE thus generated are sent to controller 205. Controller 205 acquires the amplitudes of these signals, and the shift amount to the zero level on the basis of the focus error signal FE and tracking error signal TE that have been received. Controller 205 then determines the servo signal gains (amplifications) to be applied to the focus error signal FE and the tracking error signal TE on the basis of the acquired amplitude. Controller 205 also determines the offsets of these signals on the basis of the acquired shift amount. The determined servo signal gains of the focus error signal FE and the tracking error signal TE are set to servo-signal-gain control circuits 311 and 312, respectively, and the determined offsets of these signals FE and TE are set to offset control circuits 313 and 314, respectively, shown in FIG. 17B.

FIG. 17B is a schematic diagram of a circuit that adjusts the servo signal gains and offsets of the focus error signal FE and the tracking error signal TE. This circuit is contained in signal calculating circuit 201.

Signal calculating circuit 201 includes, in addition to the circuit shown in FIG. 17A, servo-signal-gain control circuits 311 and 312, and offset control circuits 313 and 314. Servo-signal-gain control circuits 311 and 312 adjust the servo signal gains (amplifications) of the output signal of subtractor 305 (focus error signal FE) and the output signal of subtractor 306 (tracking error signal TE), respectively, under the control of controller 205. The focus error signal FE and the tracking error signal TE are amplified depending on the respectively adjusted servo signal gains, and sent to offset control circuits 313 and 314, respectively. Offset control circuits 313 and 314 adjust the offsets of the focus error signal FE and the tracking error signal TE amplified by servo-signal-gain control circuits 311 and 312, respectively, under the control of controller 205. This removes the shift to the zero level of the focus error signal FE and the tracking error signal TE, thereby generating the focus error signal FE and the tracking error signal TE from which the offsets have been removed.

The focus error signal FE and the tracking error signal TE whose offsets have been adjusted are sent to servo circuit 202. Servo circuit 202 controls object lens actuator 122 on the basis of the focus error signal FE and the tracking error signal TE that have been received.

Signal calculating circuit 201 further includes a circuit (not shown) for generating waveform signals (wobble signals) corresponding to the meandering-shaped track on the basis of the tracking error signal TE sent from offset control circuit 314. The wobble signals are generated in the same manner as, for example, in existing DVD players. The generated wobble signals are sent to servo circuit 202 and reproducing circuit 203 shown in FIG. 16, and are used for the revolution control of biosensor substrate 10 and the reproduction of the system and address information.

In the present embodiment, the servo signal gains and offsets of the focus error signal FE and the tracking error signal TE are adjusted while the excitation light is scanning the track portions corresponding to system calibration region A11. The servo signal gains and offsets are controlled by controller 205 so as to make each signal have a desired waveform and amplitude. Thus, the track portions corresponding to system calibration region A11 are scanned using the focus error signal FE and the tracking error signal TE whose servo signal gains and offsets have been adjusted. Then, the system information is acquired from the track portions corresponding to system calibration region A11. The servo signal gains and offsets thus set are used also while the excitation light is scanning the track portions corresponding to well region A12.

Figure 18A:
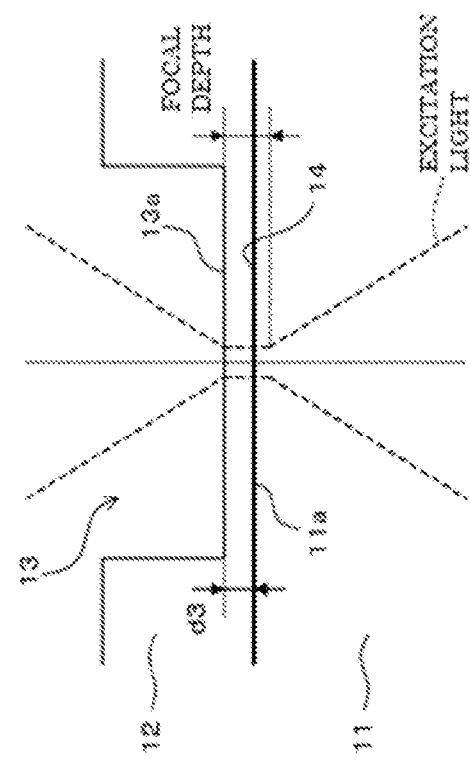
FIGS. 18A and 18B are explanatory diagrams of the focal depth of the excitation light in the third embodiment.
Figure 18B:
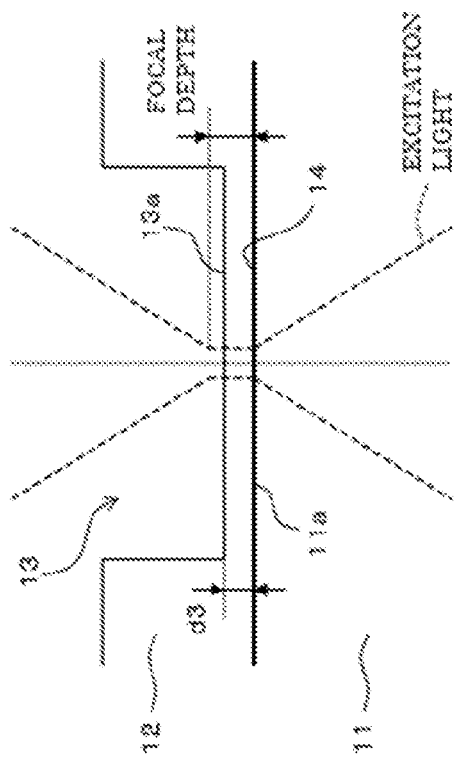

FIGS. 18A and 18B are explanatory diagrams of the focal depth of the excitation light.

As mentioned above, the excitation light has a wavelength of 405 nm and a numerical aperture (NA) of 0.34. In general, the focal depth can be calculated by the following formula: wavelength/(NA×NA). Therefore, the focal depth of the excitation light in the present embodiment is approximately 3.5 μm. The distance d3 between bottom surface portion 13a and reflective surface 11a shown in FIGS. 14A and 14B is set smaller than the focal depth of the excitation light, which is 2.0 μm in this case.

When the NA of the excitation light is set as above, the spot diameter at the focal position is approximately 1 μm. The track pitch d6 shown in FIG. 14B is set to 1 μm, which is substantially identical to the spot diameter. The nuclei of the malaria parasites each form a fluorescent spot of approximately 1 μm due to exposure to the excitation light. As a result, the excitation light spot can converge to the size of the nuclei of the malaria parasites, allowing the samples to be closely scanned with the excitation light spot, thereby ensuring the detection of the nucleus of the malaria parasites.

FIG. 18A shows the case in which the lowest point in the range of the focal depth of the excitation light coincides with the position of reflective film 14. FIG. 18B shows the case in which the highest point in the range of the focal depth of the excitation light coincides with the position of bottom surface portion 13a. Adjusting the offset voltage sent from servo circuit 202 to object lens actuator 122 can shift the focal depth of the excitation light to the back side (in the upward direction in FIG. 18A) or to somewhere in the range between FIGS. 18A and 18B from the position shown in FIG. 18A.

In the cases shown in FIGS. 18A and 18B, the distance d3 between bottom surface portion 13a of each well 13 and reflective surface 11a is 2 μm, and the focal depth of the excitation light is 3.5 μm. Consequently, both bottom surface portion 13a and reflective surface 11a are included in the range corresponding to the focal depth of the excitation light. Therefore, if the focal position of the excitation light is located on reflective surface 11a by focus servo control, the samples held on bottom surface portion 13a are also focused. Similar to the case of bottom surface portion 13a, when the excitation light is focused on reflective surface 11a in bottom surface portion 15a, bottom surface portion 15a is contained in the range of the focal depth of the excitation light.

<Effects of the Third Embodiment>

The present embodiment provides the following effects.

As shown in FIG. 14A, the portion of well layer 12 corresponding to system calibration region A11 includes recess portion 15, which are flat and do not contain wells 13. In this portion of well layer 12, no steps or no reflectance changes are caused in the scanning direction of the excitation light. Therefore, when the excitation light scans system calibration region A11, the excitation light is not scattered or reflected in different directions in well layer 12, and is allowed to be reflected in an optically stable manner from bottom surface portion 15a. Even if such reflected light is incident on light detector 109 as stray light, this stray light does not greatly affect the output signal of light detector 109 because it is applied substantially uniformly with a predetermined spread angle to the light-receiving surfaces of light detector 109. The signal component from each sensor caused by the stray light is cancelled over the course of calculation (subtraction) of the focus error signal FE and the tracking error signal TE. Therefore, the stray light has hardly any influence on the focus error signal FE and the tracking error signal TE, and also on the wobble signals generated from the tracking error signal TE. This improves the quality of the wobble signals, and hence, the reproduction accuracy of the system information.

In contrast, well region A12 includes stepped portions at the boundary of wells 13. Therefore, the excitation light incident on the stepped portions may be scattered or reflected in different directions when scanning well region A12. In the stepped portions, some of the excitation light is incident on wells 13, and other is incident on a region having no wells 13. As a result, while the excitation light is incident on the stepped portions, the reflected light is unbalanced. Thus, when the light scattered or reflected in different directions at the stepped portions or the unbalanced reflected light is incident on light detector 109 as stray light, the signal component from each sensor of light detector 109 caused by the stray light becomes unstable and disturbed. Thus, such stray light acts as large noise in the output signal of light detector 109. This noise is not cancelled over the course of calculation of the focus error signal FE and the tracking error signal TE. As a result, the stray light acts as noise also in the focus error signal FE and the tracking error signal TE, making the servo control unstable. Since the tracking error signal TE is superimposed by noise, the wobble signals generated from this signal may be degraded, thereby degrading the reproduction accuracy of the system information.

In the present embodiment, however, as described above, such problems are not caused. As a result, the system information stored in the track portions corresponding to system calibration region A11 can be acquired with high accuracy and stability.

The distance d3' between bottom surface portion 15a of recess portions 15 and reflective surface 11a is equal to the distance d3 between bottom surface portions 13a of wells 13 and reflective surface 11a. As a result, the reflected excitation light reflected by bottom surface portion 15a when system calibration region A11 is exposed to the excitation light can have substantially the same intensity as the reflected excitation light reflected by bottom surface portion 13a when well region A12 is exposed to the excitation light. Consequently, the detection signals of light detector 109 are substantially equally affected by the two beams of reflected excitation light. Thus, the application of the excitation light to system calibration region A11 facilitates the adjustment of the detection signals of light detector 109.

In the present embodiment, even if top surface layer 12b is displaced in the radial direction, unused region A13 shown in FIG. 15D prevents the track portions corresponding to system calibration region A11 from overlapping wells 13. This allows all of the system information stored in the track portions corresponding to system calibration region A11 to be acquired with high accuracy.

<Fourth Embodiment>

Figure 19A:
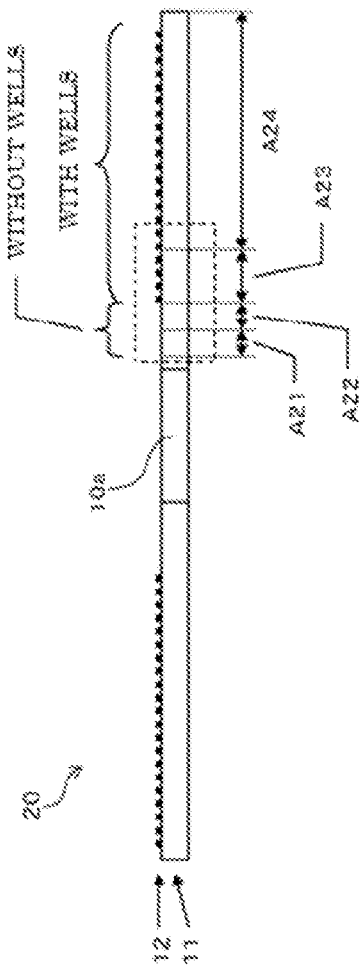
FIGS. 19A and 19B are a cross-sectional configuration and a partial perspective view, respectively, of a biosensor substrate of a fourth embodiment.

FIG. 19A is a cross-sectional configuration of biosensor substrate 20 of the present embodiment. Biosensor substrate 20 differs from biosensor substrate 10 of the third embodiment in having system region A21, calibration region A22, and empty well region A23 in place of system calibration region A11.

Biosensor substrate 20 includes system region A21, calibration region A22, empty well region A23, unused region A25, and well region A24 in this order from the center to the periphery. The portions of well layer 12 corresponding to system region A21 and calibration region A22 includes no wells 13 like the above-described system calibration region A11. Ring-shaped recess portion 15 is formed over these two regions. The portions of well layer 12 corresponding to empty well region A23 and well region A24 include a plurality of wells 13 as in biosensor substrate 10 described above.

Calibration region A22 is provided to adjust the servo signal gains and offsets of the focus error signal FE and the tracking error signal TE similar to system calibration region A11 in the third embodiment. Empty well region A23 is provided to determine whether the focus servo control and the tracking servo control are performed properly or not, and also to adjust the servo signal gains of the focus error signal FE and the tracking error signal TE. This determination and adjustment will be described later with reference to FIG. 20.

Figure 19B:
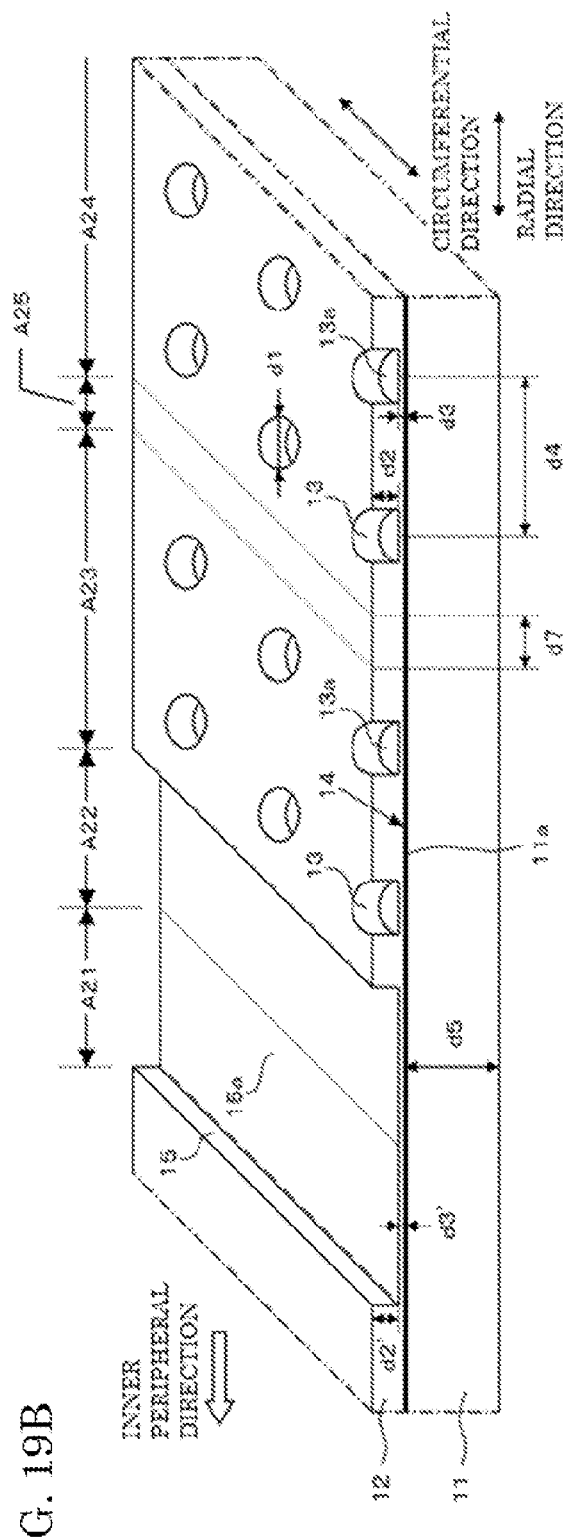

FIG. 19B is a partial perspective view of biosensor substrate 20, and more specifically, is an enlarged view of the dotted-line rectangle shown in the sectional view of FIG. 19A.

The track portions formed on the upper side (on the well layer 12 side) of base substrate 11 store the address information for locating positions on the surface of biosensor substrate 20 as in the third embodiment. The track portions corresponding to system region A21 store the system information in the data format shown in FIG. 14C as in system calibration region A11 of the third embodiment. The track portions corresponding to calibration region A22 and empty well region A23 store the dummy information in the data format shown in FIG. 14D as in unused region A25 of the third embodiment. The dummy information in this case has no particular meaning, and is, for example, "0". The entire track portions corresponding to system region A21 repeatedly store the frame shown in FIG. 14C. The entire track portions corresponding to calibration region A22 and empty well region A23 repeatedly store the frame shown in FIG. 14D.

System region A21 in the present embodiment further stores the information about the start and end positions of wells 13 in empty well region A23, and the information about the start and end positions of wells 13 in well region A24.

Figure 20:
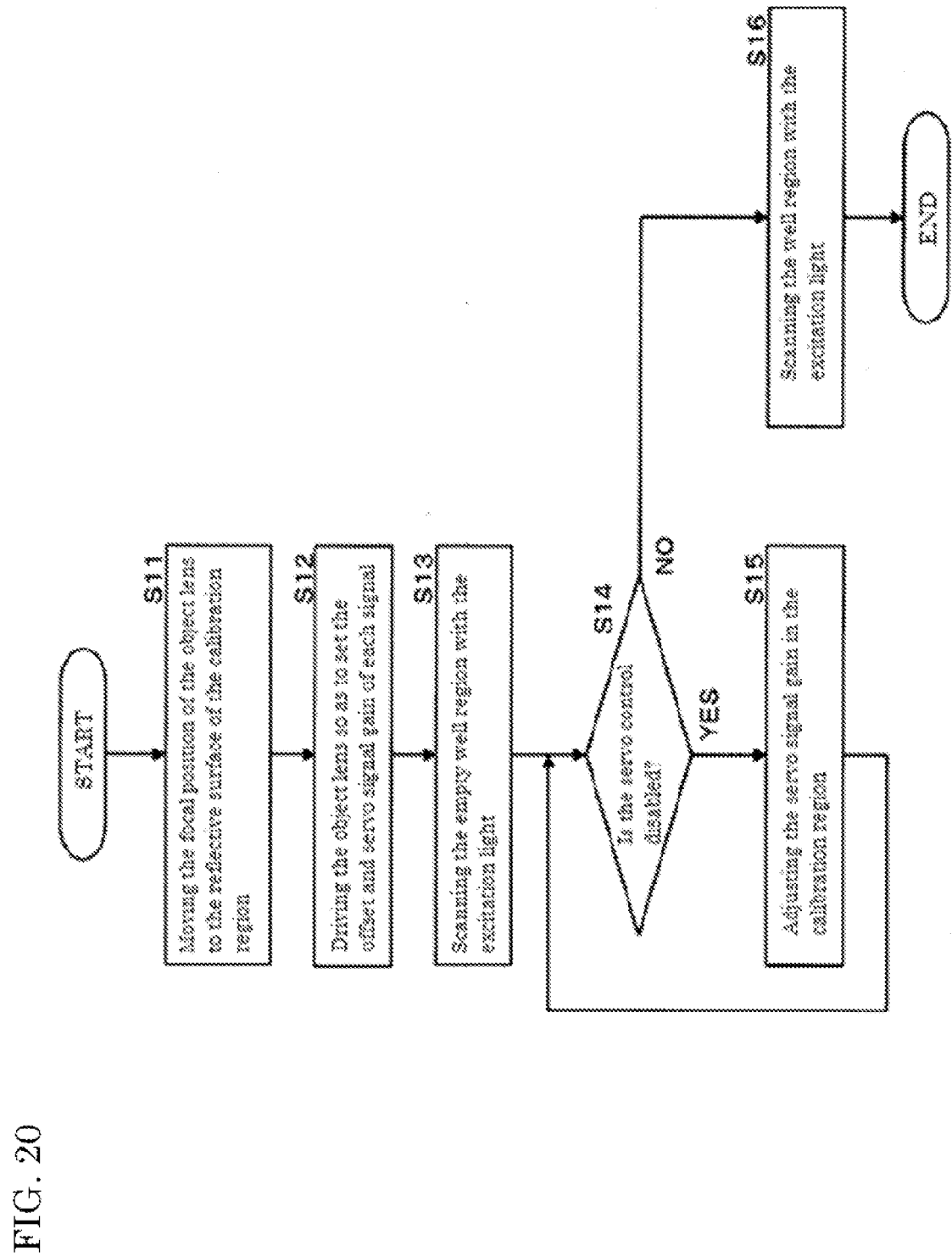
FIG. 20 is a flowchart showing how the controller sets servo signal gains and offsets of the focus error signal and the tracking error signal in the fourth embodiment.

FIG. 20 is a flowchart showing how controller 205 sets the servo signal gains and offsets of the focus error signal FE and the tracking error signal TE.

First, controller 205 rotates biosensor substrate 10, moves object lens 107 to calibration region A22, and drives object lens actuator 122 so as to focus the excitation light on the track portions on reflective surface 11a corresponding to calibration region A22 (S11).

At this moment, controller 205 performs a focus search with object lens 107. When the focus search ends, controller 205 turns the focus servo control ON and then turns the tracking servo control ON. Controller 205 sets the servo signal gains and offsets of the focus error signal FE and the tracking error signal TE on the basis of the focus error signal FE obtained at the focus search, and the tracking error signal TE obtained during the time after the focus servo control is turned on and before the tracking servo control is turned on (S12). More specifically, controller 205 determines the servo signal gain and offset of the focus error signal FE on the basis of the S-curve amplitude and the shift amount to the zero level of the focus error signal FE. Controller 205 further determines the servo signal gain and offset of the tracking error signal TE on the basis of the amplitude and the shift amount to the zero level of the tracking error signal TE. Controller 205 then sets the determined servo signal gains to servo-signal-gain control circuits 311 and 312, respectively, and the determined offsets to offset control circuit 313 shown in FIG. 17B.

After the servo signal gains and offsets are set in this manner, the wobble signals are reproduced from the track portions corresponding to system region A21, and the system information is acquired from the reproduced wobble signals.

Next, controller 205 moves object lens 107 toward the outer periphery, and allows the excitation light to scan a predetermined region including wells 13 in empty well region A23 in the radial direction with the servo signal gains and offsets set in S12 (S13). Controller 205 then determines whether the focus servo control or the tracking servo control is disabled during this scan (S14). Whether the focus servo control is disabled or not is determined by, for example, whether the focus servo control is disabled for a predetermined time or not. Whether the tracking servo control is disabled or not is determined by, for example, whether desired address information (subsequent to the address information acquired before the servo control is disabled) is unavailable for a predetermined time or not.

The focus servo control or the tracking servo control is disabled (S14: YES), controller 205 allows the excitation light again to scan a predetermined region including wells 13 in calibration region A22 in the radial direction. In the meantime, controller 205 adjusts the servo signal gains set in S21 to prevent the focus servo control and the tracking servo control from being disabled (S15). More specifically, controller 205 sets the servo signal gains of the focus error signal FE and the tracking error signal TE (the gains obtained from servo-signal-gain control circuits 311 and 312) smaller by predetermined amounts than the values set in S12. Then, the process returns to S14 to determine again whether the focus servo control and the tracking servo control are disabled or not. The determination in S14 is performed by scanning sufficiently long track portions. The determination is executed, for example, until the change in the address information since the scan start reaches a predetermined value. In the meantime, if the servo control is not disabled, the determination result in S14 is "NO".

When "NO" in S14, controller 205 allows the excitation light to scan well region A24 with the servo signal gain set in S12 and the servo signal gain set in S12 or S15 (S16), and starts measuring the samples held in wells 13. This terminates the process of setting the servo signal gains and offsets of the focus error signal FE and the tracking error signal TE.

<Effects of the Fourth Embodiment>

Similar to the third embodiment, in the present embodiment, the system information stored in the track portions corresponding to system region A21 can be acquired with high accuracy. This allows accurate acquisition of systematically necessary information such as the condition of biosensor substrate 10 set on fluorescence detection device 1; wells 13 to be detected; positions to be accessed. In particular, it is possible to correctly read the contents stored in the system region, allowing an expired biosensor substrate to be removed from the device, or a warning to be issued to the user. Appreciating the system information facilitates the determination of whether the biosensor substrate corresponds to the device or not, thereby limiting the use of an inappropriate biosensor substrate.

After the servo signal gains and offsets are set in calibration region A22 and before the measurement of the samples is actually started, it is tested whether the servo control is disabled or not in empty well region A23 having the same structure as well region A24, using the servo signal gains and offsets set in calibration region A22. If the servo control is disabled, the servo signal gains are adjusted again to prevent the servo control from being disabled while empty well region A23 is scanned. This makes the servo control less likely to be disabled during the actual measurement of the samples. As a result, the sample measurement is facilitated, preventing the samples from being exposed to the excitation light either too strong or for too long a time. This prevents the samples from being degraded by the excitation light.

In disc-shaped biosensor substrates 10 and 20 as in the third and fourth embodiments, a surface run-out occurs relatively less frequently on the inner peripheral side, so that signals can be acquired more easily. For this reason, system calibration region A11 in the third embodiment and system region A21 and calibration region A22 in the fourth embodiment are formed on the inner peripheral side of biosensor substrates 10 and 20, respectively, as shown in FIG. 13 and FIG. 19A. Alternatively, however, these regions may be formed either on the outer peripheral side of biosensor substrates 10 and 20 or between the inner and outer peripheries. In the fourth embodiment, the region including system region A21 and calibration region A22 is not necessarily adjacent to empty well region A23. For example, the region including system region A21 and calibration region A22; well region A24; and empty well region A23 may be formed in this order from the center to the periphery.

Noise does not easily superimpose the detection signals of light detector 109 while the excitation light is scanning system calibration region A11 or calibration region A22. Therefore, these detection signals may be used to adjust other settings than the servo signal gains and offsets. For example, the detection signals may be used to detect warpage of biosensor substrates 10 and 20, thereby performing tilt adjustment for either object lens 107 or the optical system including object lens 107 depending on the warpage. In this case, the warpage increases toward the outer periphery. Therefore, calibration region A22 may be formed in each of the inner, middle, and outer peripheries, and tilt adjustment in the entire regions may be adaptively performed depending on the warpage detected in the respective calibration regions A22.

In the third and fourth embodiments, system calibration region A11 and system region A21 are formed on the inner peripheral side of biosensor substrates 10 and 20, respectively. The reason for this is to reduce the warpage and surface run-out of biosensor substrates 10 and 20. These regions, however, may be formed in an arbitrary area other than the inner peripheral side. In that case, it is preferable that the portions of well layer 12 corresponding to system calibration region A11 and system region A21 either do not include wells or include recess portions in order to reduce the influence of wells.

In the third and fourth embodiments, the track is formed of grooves, but may alternatively be formed of a pit string as in an existing CD, or a combination of a pit string and grooves. More specifically, the track portions corresponding to system calibration region A11 of the third embodiment and those corresponding to system region A21 and calibration region A22 of the fourth embodiment may be formed of a pit string, whereas the track portions corresponding to well regions A12 and A24 may be formed of grooves. Alternatively, the track portions corresponding to system calibration region A11 of the third embodiment and those corresponding to system region A21 and calibration region A22 of the fourth embodiment may be formed of grooves, whereas the track portions corresponding to well regions A12 and A24 may be formed of a pit string.

It is preferable that the track portions corresponding to empty well region A23 shown in FIG. 19B be formed in the same manner as well region A24. For example, in the case that the track portions corresponding to system region A21 are formed of a pit string and those corresponding to well region A24 is formed of grooves, it is preferable that the track portions corresponding to empty well region A23 be formed of grooves. Thus, when track portions corresponding to empty well region A23 and well region A24 are made of the same configuration, the servo signal gains and offsets adjusted in empty well region A23 can be easily optimized also in well region A24.

In the third and fourth embodiments, recess portions 15 are formed on the portions of well layer 12 corresponding to system calibration region A11 and system region A21. Alternatively, however, the portions of well layer 12 may not include recess portions 15, so that the upper surface of well layer 12 of system calibration region A11 and system region A21 can be flush with the upper surface of the portions of well layer 12 corresponding to the other regions. However, in the case that the acquisition of the system information and the adjustment of the focus error signal FE and the tracking error signal TE are performed in system calibration region A11 as in the third embodiment, the following configuration can provide better adjustment because noise occurring at the time of detecting wells 13 can be added. The portion of well layer 12 corresponding to system calibration region A11 has bottom surface portion 15a, which is away from reflective surface 11a by the distance d3 as shown in FIG. 14A, and bottom surface portion 15a is made as high as bottom surface portions 13a of wells 13.

In the third embodiment, as shown in FIG. 14A, the portion of well layer 12 corresponding to unused region A13 includes bottom surface portion 15a, but may alternatively include a flat surface flush with the upper surface of well region A12.

In the third embodiment, as shown in FIG. 19B, the portion of well layer 12 corresponding to unused region A25 includes a flat surface flush with the upper surface of well region A24, but may alternatively include a bottom surface portion flush with bottom surface portion 15a.

In the third and fourth embodiments, the portions of well layer 12 corresponding to system calibration region A11 and system region A21 include ring-shaped recess portions 15; alternatively, however, recess portions 15 may be formed only part of the perimeter. For example, concentrically arranged wells 13 may be absent only in a predetermined area in the radial direction, and instead, recess portions 15 having bottom surface portion 15a may be formed in this area.

In the fourth embodiment, the wells formed in empty well region A23 of well layer 12 have the same size as wells 13 formed in well region A24, but may alternatively have a different size. For example, the wells in empty well region A23 may have a different diameter from wells 13 of well region A24. In this case, however, it is preferable that the noise occurring when the excitation light scans empty well region A23 be substantially the same as noise occurring when the excitation light scans well region A24. It is therefore preferable that the wells of empty well region A23 have the same shape as those in well region A24. For example, it is preferable that the bottom surface portion of the wells in empty well region A23 has the same height (the distance from reflective surface 11a) as bottom surface portions 13a of wells 13 of well region A24.

In the case that empty well region A23 includes wells different in size from those in well region A24, the wells in empty well region A23 may be formed so that the noise occurring when empty well region A23 is scanned may be larger than in well region A24. As a result, well region A24 can be scanned with the parameters such as the servo signal gains adjusted in empty well region A23 that has large noise. This ensures the detection of signals from the wells in well region A24.

In the fourth embodiment, as shown in FIG. 20, the servo signal gains and offsets of the focus error signal FE and the tracking error signal TE are set in calibration region A22 (S12), and the servo signal gains are set again in empty well region A23 (S15). Instead of this, controller 205 may allow the servo signal gains and offsets of the focus error signal FE and the tracking error signal TE to be set on the basis of the previously stored servo signal gains and offsets (S12), and may allow the set servo signal gains to be set again in empty well region A23 (S15).

In the fourth embodiment, as shown in S14 and S15 of FIG. 20, the servo signal gains of the focus error signal FE and the tracking error signal TE are set again while empty well region A23 is scanned so as to prevent the servo control from being disabled. Instead, however, even when the servo control is not disabled while empty well region A23 is scanned, controller 205 may finely adjust the servo signal gains of the focus error signal FE and the tracking error signal TE so as to make each signal has a desired waveform and amplitude.

The embodiments of the present invention have been described as above, but the present invention is not limited to these embodiments, and can be modified and implemented in various forms.

In the embodiments described as above, the biosensor substrate is one example of a sample holding carrier described in the claims, and the well is one example of sample accommodation units or a structural portion described in the claims.

For example, in the above embodiments, it is determined whether the erythrocytes held in wells 13 are infected with malaria parasites or not. However, the samples to be held in wells 13 and the target to be detected are not limited to erythrocytes.

For example, it is possible to detect from various groups of cells a cell expressing a specific gene; a cell excess or deficient in a biological material such as nucleic acid, protein, lipid, or sugar as a specific cell. Such a specific cell may be a cell either found in nature or produced artificially. Examples of the cells found in nature include pathogenic cells; diseased cells; cells infected with pathogens or pathogenic organisms; mutant cells; and unknown cells with specific behaviors. Examples of the artificial treatment include physical treatments (e.g., electromagnetic irradiation), chemical treatments (e.g., drug treatments), and engineered treatments (e.g., gene recombination).

It is also possible to subject a group of cells to one of the artificial treatments whose influence on cells is known, and to detect, as specific cells, those cells not affected by the influence or those more affected than others by the influence. The specific cells can be, for example, cells resistant or highly sensitive to a drug treatment.

The type of the group of cells is not particularly limited. For example, it can be a group of unicellular organisms or a group of cells originated from multicellular organisms. The cells originated from multicellular organisms can be, for example, cells obtained from normal or pathological tissue of living things, or cultured cells originated from these cells. The living things from which these cells are obtained are not particularly limited. The target cells may be obtained from, for example, animals or plants. More specifically, they may be obtained from vertebrates (mammals and birds in particular), insects, or may be plant-cultured cells. However, the target cells are not limited to these, and may be a group of cells of the same type or of different types.

In the above embodiments, reflective film 14 is made of metal, but alternatively be made of a transparent dielectric material. In the latter case, reflection can be generated by making the refractive index of base substrate 11 different from that of the dielectric material. More specifically, base substrate 11 can be made of polycarbonate (refractive index: 1.59), and reflective film 14 can be made of $TiO_2$ (refractive index: 2.65) or ZnO (refractive index: 2.2). In the case of using these dielectric materials, it is preferable that the thickness of reflective film 14 be 10 nm to 150 nm in order to obtain sufficient reflectance. The thickness is more preferably 10 nm to 45 nm in terms of the production cost and the positional relationship between the reflective film and the well bottom surface. When made of niobium dioxide ($Nb_2O_5$), reflective film 14 can have a high reflectance in the vicinity of wavelength 400 nm, a low reflectance in the vicinity of wavelength 500 nm, thereby having a high reflectance R1 of the excitation light, and a low reflectance R2 of the fluorescence. Thus, when the relation the reflectance R1>the reflectance R2 is satisfied, the servo performance can be improved so as to achieve more fluorescence detection. Reflective film 14 may alternatively have a laminated structure of a dielectric film and a metal film.

In the above embodiments, as shown in FIGS. 1 and 13, wells 13 have a columnar hollow, but the hollow may alternatively be rectangular prismatic, elliptical columnar, conical, or have any other shapes as long as the samples can be held. The dimensions d1 to d7 are not limited to the values set in the above embodiments, and can be arbitrarily determined. The address length of reflective surface 11a may be set by various methods as long as it can identify the positions of wells 13.

In the above embodiments, the wavelength of the excitation light emitted from semiconductor laser 101 is set to 405 nm, but may be arbitrarily set depending on the type of the fluorescent label used in the samples to be measured. The various parameters of the optical system such as the transmission wavelength range of dichroic prism 106 may be arbitrarily changed with changes in the excitation light and the fluorescence wavelength. In the above embodiments, the NA of the excitation light is set to 0.34, but may be arbitrarily set depending on the size of the samples to be measured. The NA of object lens 107 is preferably as large as possible to increase the amount of light to be detected. In the case of using other types of fluorescent labels, it is preferable that the fluorescence wavelength be at least 30 nm away from the excitation light. If closer to the fluorescence wavelength than this, the excitation light cannot be completely separated by the dichroic prism or the like, and becomes noise in the fluorescence detection.

In the above embodiments, the track is composed of grooves, but may alternatively be formed of a pit string, or a combination of a pit string and grooves.

In the above embodiments, biosensor substrate 10 is formed by injection molding base substrate 11, depositing reflective film 14 on the upper surface of reflective surface 11a, spin-coating bottom surface layer 12a, and forming top surface layer 12b by 2P molding. The method of forming biosensor substrate 10 is not limited to this, and may be formed by other methods if necessary.

In the above embodiments, it is possible to provide a lid over wells 13 at the time of rotating biosensor substrate 10 on rotation device 12. This prevents undesired (unintended) outflow, evaporation, or transfer of the samples from wells 13.

Figure 21A:
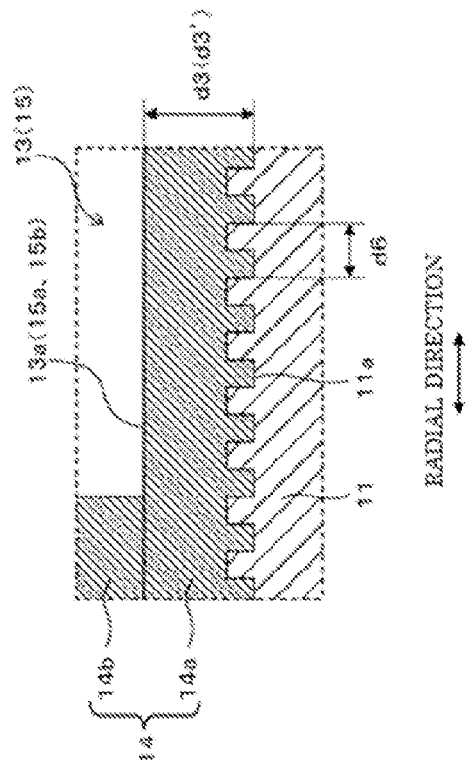
FIGS. 21A-21C are other configurations of wells than those in the first to fourth embodiments.
Figure 21B:
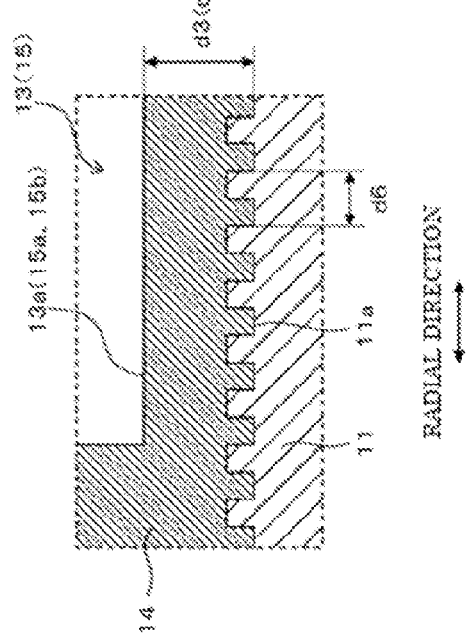

In the above embodiments, well layer 12 is formed on reflective film 14; alternatively, however, reflective film 14 itself may function as well layer 12. In other words, as shown in FIG. 21A, reflective film 14 formed on the upper surface of base substrate 11 may be provided with a plurality of minuscule wells 13 and grooves 15. In this case, reflective film 14 only needs to be a material such as a resin material, having a different refractive index from base substrate 11. Furthermore, reflective film 14 shown in FIG. 21A may be composed of bottom surface layer 14a and top surface layer 14b as shown in FIG. 21B. Bottom surface layer 14a and top surface layer 14b may be made of different materials from each other. In addition, the samples may be dropped directly into the wells, but may alternatively be dropped through injection holes provided separately. In this case, the samples are made to flow into the wells along the well layer or sample introduction portions such as microchannels formed above the well layer, and are prevented from flowing into the fluorescent region or the empty well region.

Figure 21C:
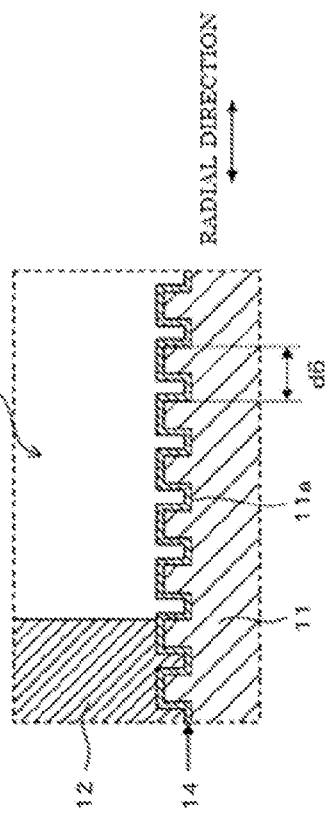

In the above embodiments, well layer 12 formed on reflective film 14 includes wells 13 having bottom surface portion 13a; grooves 15 having fluorescent bottom surface portion 15a; and grooves 15 having non-fluorescent bottom surface portion 15b. Alternatively, however, bottom surface portion 13a, fluorescent bottom surface portion 15a, and non-fluorescent bottom surface portion 15b may compose the upper surface of reflective film 14. In other words, as shown in FIG. 21C, wells 13 may be composed of through-holes formed in well layer 12, and be formed on reflective film 14. In this case, the well layer may be formed by bonding a perforated sheet made of a resin such as PMMA instead of ultraviolet curable resin.

In the second embodiment, the focal position of the excitation light is located on fluorescent bottom surface portion 15a by moving collimator lens 104 along the optical axis of the excitation light, but may alternatively be located by adjusting the offset voltage sent to object lens actuator 122 as described with reference to FIGS. 7A and 7B.

In the first and second embodiments, biosensor substrate 10 is disc-shaped, but may alternatively be rectangular.

Figure 22:
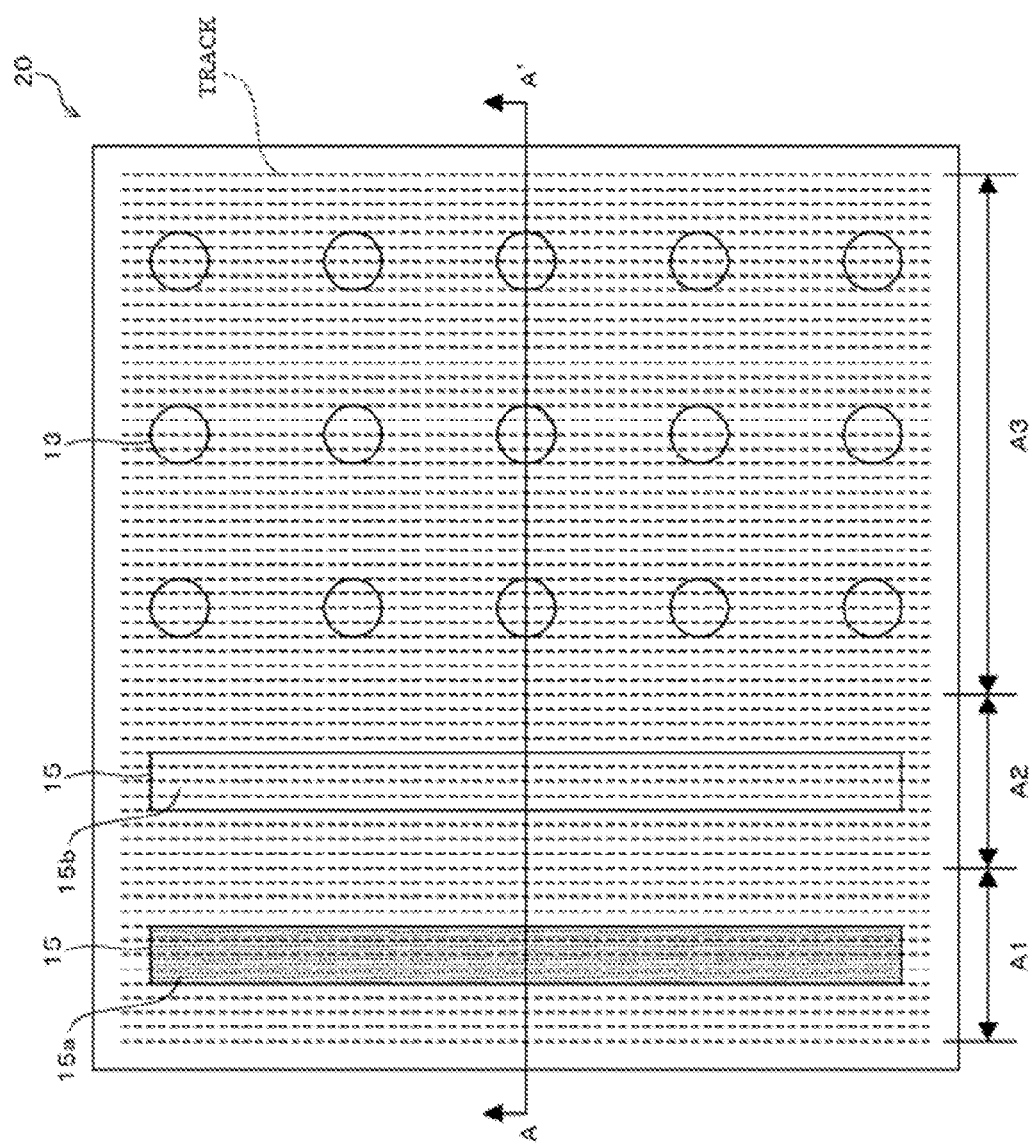
FIG. 22 is a schematic configuration of the rectangular biosensor substrate of the first and second embodiments.

FIG. 22 is a schematic configuration of rectangular biosensor substrate 20. In FIG. 22, biosensor substrate 20 is seen from the upper surface side. In this configuration example, as shown in FIG. 22, biosensor substrate 20 is provided with a plurality of linear tracks (grooves) at a predetermined pitch. Furthermore, wells 13 and grooves 15 are formed in parallel with the tracks. The other configurations of biosensor substrate 20 are identical to those of the above embodiments. The cross section of biosensor substrate 20 taken along line A-A' is identical to that shown in FIG. 2A. As in the above embodiments, the grooves store address information.

In this configuration example, biosensor substrate 20 and object lens 107 are moved relatively in the direction parallel to the tracks. At this moment, biosensor substrate 20 can be fixed, and the optical system including semiconductor laser 101 to fluorescence detector 111, and the housing accommodating holder 121, object lens actuator 122, and lens actuators 124 and 125 can be moved in the direction parallel to the tracks along the guide shaft. During this time, in the same manner as in the above embodiments, object lens 107 is subjected to a focus control and a tracking control so that the beam spot of the excitation light is moved along a single track. When the beam spot is moved to the end of the single track, object lens 107 is moved by the distance corresponding to the track pitch to the direction perpendicular to the tracks, thereby performing a jump to the next track. After this, the housing is moved in the direction parallel to the tracks so as to scan the next track. Thus, when the predetermined number of tracks has been scanned, biosensor substrate 20 is moved in the direction perpendicular to the tracks so that object lens 107 is returned to the neutral position. Hereinafter, the same operation is repeated until all the tracks are scanned.

In this configuration example, in the same manner as in the above embodiments, the fluorescent signal gain factor G and the threshold Vsh are set. This improves the accuracy of the determination of whether the erythrocytes are infected with malaria parasites or not. This makes it possible to accurately acquire only the fluorescence generated in the erythrocytes infected with malaria parasites.

In the third and fourth embodiments, biosensor substrate 10 is disc-shaped, but may alternatively be rectangular.

Figure 23:
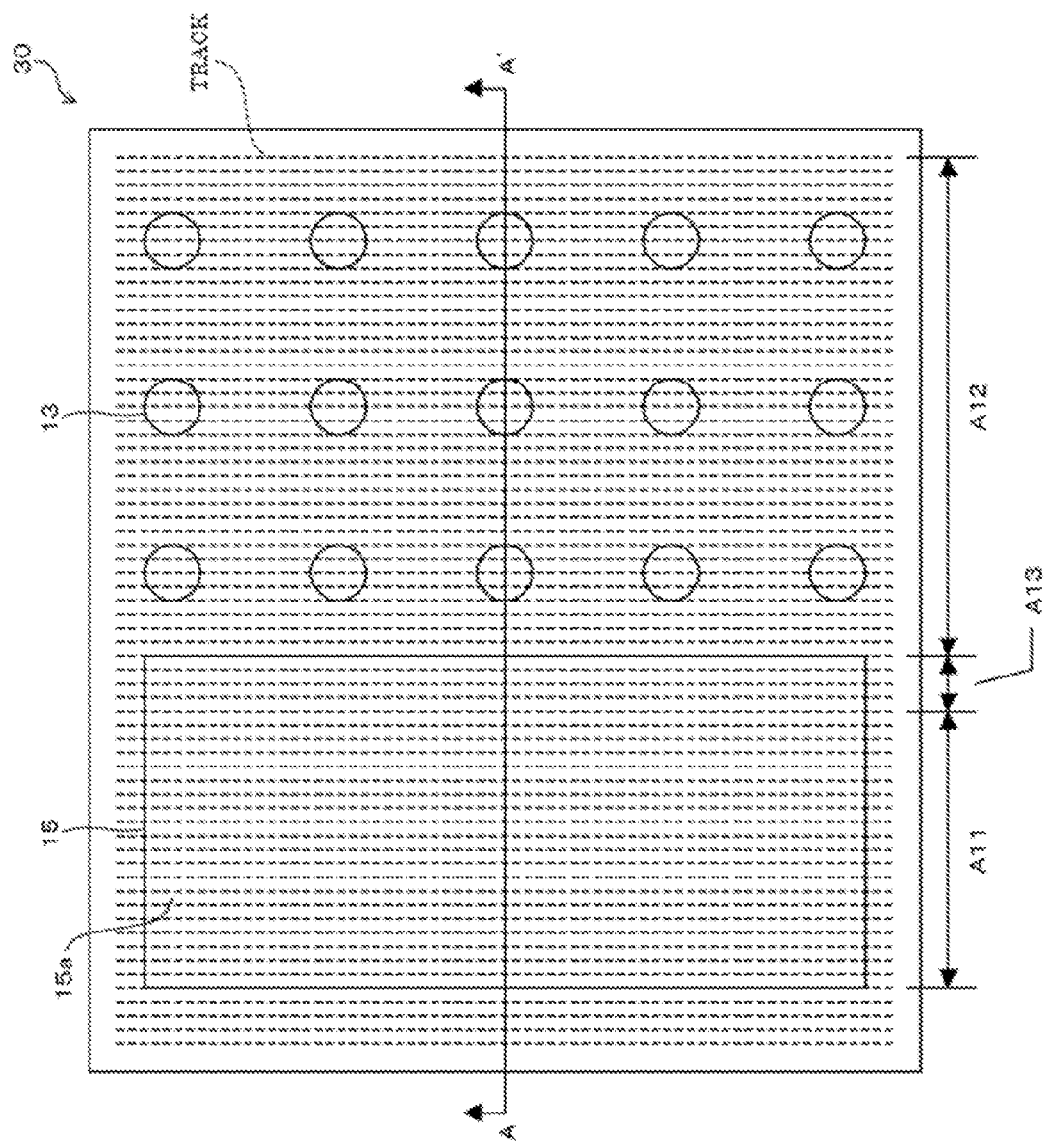
FIG. 23 is a schematic configuration of the rectangular biosensor substrate of the third and fourth embodiments.

FIG. 23 is a schematic configuration of rectangular biosensor substrate 20. In FIG. 23, biosensor substrate 30 is seen from the upper surface side.

In this configuration example, as shown in FIG. 23, biosensor substrate 30 is provided with a plurality of linear tracks at a predetermined pitch. Furthermore, wells 13 and recess portion 15 are formed in parallel with the tracks. The other configurations of biosensor substrate 30 are identical to those of the third embodiment. The cross section of biosensor substrate 30 taken along line A-A' is identical to that shown in FIG. 14A. As in the third embodiment, the tracks store address information, and the tracks corresponding to system calibration region A11 store system information.

In this configuration example, biosensor substrate 30 and object lens 107 are moved relatively in the direction parallel to the tracks. At this moment, biosensor substrate 30 can be fixed, and the optical system including semiconductor laser 101 to fluorescence detector 111, and the housing accommodating holder 121 and object lens actuator 122 can be moved in the direction parallel to the tracks along the guide shaft. During this time, in the same manner as in the above embodiments, object lens 107 is subjected to a focus control and a tracking control so that the beam spot of the excitation light is moved along a single track. When the beam spot is moved to the end of the single track, object lens 107 is moved by the distance corresponding to the track pitch to the direction perpendicular to the tracks, thereby performing a jump to the next track. After this, the housing is moved in the direction parallel to the tracks so as to scan the next track. Thus, when the predetermined number of tracks has been scanned, biosensor substrate 30 is moved in the direction perpendicular to the tracks so that object lens 107 is returned to the neutral position. Hereinafter, the same operation is repeated until all the tracks are scanned.

In this configuration example, in the same manner as in the third embodiment, the system information stored in the track portions corresponding to system calibration region A11 can be accurately acquired. Biosensor substrate 30 may be configured to have the same cross section taken along line A-A' as that shown in FIG. 19B. In this case, as in the fourth embodiment, it is possible to accurately acquire the system information stored in the track portions corresponding to system region A21, and it is tested whether the servo control is not disabled in calibration region A22. This prevents the samples from being exposed too much to the excitation light, and establishes stable servo control, thereby facilitating sample measurement.

In the above embodiments, the excitation light is applied from the bottom side of base substrate 11, but may be applied from the upper surface side of base substrate 11. In the latter case, the excitation light is directly applied to the samples held in wells 13 without passing through base substrate 11. It is preferable that the height d2 of wells 13 be small enough to make the excitation light reach reflective film 14 even if the excitation light applied to wells 13 is attenuated by the samples held in wells 13. In fluorescent region A1, it is preferable that the fluorescent material be coated on the surface appropriately formed between the height of bottom surface portion 13a and the height of planar portions 16 depending on the type of the test object and the height of wells 13. In the first and second embodiments, the upper limit of the fluorescent signal gain G is previously set. However, in the case of considering the production tolerance of the biosensor substrate, the upper limit of the fluorescent signal gain G or a predetermined value may be previously stored in the system region of the substrate.

In the embodiments of the present invention, various changes are possible within the scope of the technical idea shown in the claims. For example, the configuration of the above embodiment 1 can be changed, by combining with the configuration of the above embodiment 3, to the configuration that has both fluorescent region and system calibration region.

It is possible to extract from the configuration shown in FIGS. 19A and 19B, the following aspect of the present invention which does not include the limitations concerning system region A21 (corresponding to the "first region" in the claims).

(1) A sample holding carrier including:
a substrate;
a track formed on a first surface side of the substrate; and
a plurality of sample accommodation units formed on the first surface side of the substrate,
wherein the first surface side of the substrate is provided with a region having the sample accommodation units and a structural portion region having a plurality of structural portions not holding samples.

(2) A fluorescence detection device that irradiates a sample holding carrier holding a fluorescently-labeled sample with irradiation light and detects fluorescence yielded from the sample irradiated with the irradiation light, wherein the sample holding carrier includes: a substrate; a track formed on a first surface side of the substrate; and a plurality of sample accommodation units formed on the first surface side of the substrate, wherein the first surface side of the substrate is provided with a region having the sample accommodation units and a structural portion region having a plurality of structural portions not holding samples,
wherein the fluorescence detection device includes:
a light source for emitting the irradiation light;
an object lens for converging the irradiation light on the sample holding carrier;
a light detector for receiving the irradiation light reflected by the sample holding carrier;
a fluorescence detector for receiving fluorescence generated from the samples by exposure to the irradiation light; and
a parameter setting unit for setting a predetermined parameter to be used to scan the sample accommodation units based on a signal sent form the light detector when the irradiation light is applied to the structural portion region.

In the above aspects (1) and (2) of the invention, the parameter values used to scan the sample accommodation units can be appropriately set by applying irradiation light to the structural portion region.

What is claimed is:
1. A sample holding carrier comprising:
a substrate having a disk shape;
a plurality of sample accommodation units arranged on a first surface side of the substrate; and
a fluorescent portion on which a fluorescent material is disposed, the fluorescent portion arranged on the first surface side of the substrate and generating fluorescence under exposure to irradiation light,
wherein the fluorescent portion is separated from the plurality of sample accommodation units in a radial direction of the substrate, the entire fluorescent portion being disposed in a first radial region and each of the plurality of sample accommodation units being disposed in a second radial region, the fluorescent portion not containing any sample accommodation units, and
wherein the first radial region and the second radial region do not overlap with one another.

2. The sample holding carrier according to claim 1, further comprising a reflective film that is arranged on the first surface side of the substrate to partially reflect the irradiation light,
wherein the fluorescent portion has a bottom surface coated with a material generating fluorescence under exposure to the irradiation light.

3. The sample holding carrier according to claim 1, further comprising a non-fluorescent portion on which the fluorescent material is not disposed, the non-fluorescent portion arranged on the first surface side of the substrate and is separated from the sample accommodation units and the fluorescent portion in the radial direction of the substrate, the non-fluorescent portion having a bottom surface not coated with a material generating fluorescence.

4. A sample holding carrier according to claim 1, further comprising a track formed on a first surface side of the substrate,
wherein the first surface side of the substrate is provided with a first region not including the sample accommodation units and a second region including the sample accommodation units; and
system information is stored in the track at a portion corresponding to the first region.

5. The sample holding carrier according to claim 4, further comprising a reflective film that is arranged on the track of the substrate to partially reflect the irradiation light,
wherein the first region is a recess portion lower than the second region; and
a bottom surface of the sample accommodation units and a bottom surface of the recess portion are nearly equidistant from the reflective film.

6. The sample holding carrier according to claim 4, further comprising a third region disposed between the first region and the second region and not including the sample accommodation units,
wherein system information is not stored in the track at a portion corresponding to the third region.

7. The sample holding carrier according to claim 4, further comprising a fourth region disposed separately from the second region and including a plurality of structural units not holding samples.

8. The sample holding carrier according to claim 1, wherein the fluorescent portion is disposed near an inner periphery of the substrate.

9. The sample holding carrier according to claim 1, wherein the fluorescent portion is disposed near an outer periphery of the substrate.

10. The sample holding carrier according to claim 1, wherein the fluorescent material is an inorganic fluorescent material.

11. The sample holding carrier according to claim 1, wherein the fluorescent material is disposed in a ring-shaped pattern.

12. The sample holding carrier according to claim 1, further comprising:
a lid provided over the sample accommodation units.

13. A fluorescence detection device that irradiates a sample holding carrier holding a fluorescently-labeled sample with irradiation light and detects fluorescence yielded from the sample irradiated with the irradiation light,
wherein the sample holding carrier comprises:
a substrate having a disk shape;
a plurality of sample accommodation units arranged on a first surface side of the substrate; and
a fluorescent portion on which a fluorescent material is disposed, the fluorescent portion arranged on the first surface side of the substrate and is separated from the sample accommodation units in a radial direction of the substrate, the entire fluorescent portion being disposed in a first radial region and each of the plurality of sample accommodation units being disposed in a second radial region, the first radial region and the second radial region do not overlap with one another, the fluorescent portion not containing any sample accommodation units, and the fluorescent portion generating fluorescence under exposure to the irradiation light;

the fluorescence detection device comprising:

a light source for emitting the irradiation light;

an object lens for converging the irradiation light on the sample holding carrier;

a fluorescence detector for receiving the fluorescence generated from the samples or from the fluorescent portion by exposure to the irradiation light; and an amplification rate setting unit for setting amplification rate of a signal sent from the fluorescence detector based on the signal sent from the fluorescence detector when the fluorescent portion is exposed to the irradiation light.

14. The fluorescence detection device according to claim 13,
wherein the sample holding carrier further comprises a non-fluorescent portion on which the fluorescent material is not disposed, the non-fluorescent portion arranged on the first surface side of the substrate and is separated from the sample accommodation units and the fluorescent portion in the radial direction of the substrate, the non-fluorescent portion having a bottom surface not coated with a material generating the fluorescence, the fluorescence detection device further comprising a threshold setting unit for setting a threshold to detect the fluorescence generated in the samples, the threshold being applied to a signal sent from the fluorescence detector based on the signal sent from the fluorescence detector when the non-fluorescent portion is exposed to the irradiation light.

15. The fluorescence detection device according to claim 13, further comprising:
a condenser lens for collecting the fluorescence on the fluorescence detector;
a lens actuator for driving the condenser lens along an optical axis of the condenser lens; and
a lens control unit for driving the lens actuator so as to increase a magnitude of the signal sent from the fluorescence detector when the fluorescent portion is exposed to the irradiation light.

16. The fluorescence detection device according to claim 13, wherein the fluorescent material is disposed in a ring-shaped pattern.

17. The fluorescence detection device according to claim 8, further comprising:
a lid provided over the sample accommodation units.

18. A sample holding carrier comprising:
a substrate;
a plurality of sample accommodation units arranged on a first surface side of the substrate;
a fluorescent portion arranged on the first surface side of the substrate and is separated from the sample accommodation units in a radial direction of the substrate, the entire fluorescent portion being disposed in a first radial region and each of the plurality of sample accommodation units being disposed in a second radial region, the first radial region and the second radial region do not overlap with one another, the fluorescent portion not containing any sample accommodation units, and the fluorescent portion having a bottom surface coated with a fluorescent material generating fluorescence under exposure to irradiation light; and
a reflective film that is arranged on the first surface side of the substrate to partially reflect the irradiation light;
wherein the bottom surface of the fluorescent portion and a bottom surface of the sample accommodation units are equidistant from the reflective film.

19. The sample holding carrier according to claim 18, wherein the fluorescent material is disposed in a ring-shaped pattern.

* * * * *